US008822703B2

(12) United States Patent
Krzyzaniak et al.

(10) Patent No.: US 8,822,703 B2
(45) Date of Patent: Sep. 2, 2014

(54) SALT FORMS OF [R-(R*,R*)]-2-(4-FLUOROPHENYL)-BETA,DELTA-DIHYDROXY-5-(1-METHYLETHYL)-3-PHENYL-4[PHENYLAMINO) CARBONYL]-1H-PYRROLE-1-HEPTANOIC ACID

(71) Applicant: Pfizer Inc., New York, NY (US)

(72) Inventors: Joseph Francis Krzyzaniak, Pawcatuck, CT (US); Jason Albert Leonard, New Rochelle, NY (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/016,839

(22) Filed: Sep. 3, 2013

(65) Prior Publication Data

US 2014/0005384 A1    Jan. 2, 2014

Related U.S. Application Data

(62) Division of application No. 13/537,432, filed on Jun. 29, 2012, now Pat. No. 8,552,207, which is a division of application No. 12/966,488, filed on Dec. 13, 2010, now Pat. No. 8,236,966, which is a division of application No. 11/579,656, filed as application No. PCT/IB2005/001237 on Apr. 25, 2005, now Pat. No. 7,875,731.

(60) Provisional application No. 60/568,379, filed on May 5, 2004.

(51) Int. Cl.
C07D 207/00      (2006.01)

(52) U.S. Cl.
USPC ........................................................ 548/537

(58) Field of Classification Search
USPC ........................................................ 548/537
See application file for complete search history.

(56) References Cited

U.S. PATENT DOCUMENTS

| 4,681,893 A | 7/1987 | Roth et al. |
| 5,003,080 A | 3/1991 | Butler et al. |
| 5,273,995 A | 12/1993 | Roth et al. |
| 5,342,952 A | 8/1994 | Butler et al. |
| 5,969,156 A | 10/1999 | Briggs et al. |
| 6,087,511 A | 7/2000 | Lin et al. |
| 6,121,461 A | 9/2000 | McKenzie |
| 6,274,740 B1 | 8/2001 | Lin et al. |
| 6,583,295 B1 | 6/2003 | Pflaum |
| 7,056,942 B2 | 6/2006 | Hildesheim et al. |
| 7,875,731 B2 | 1/2011 | Campeta et al. |
| 8,552,207 B2 * | 10/2013 | Krzyzaniak et al. .......... 548/537 |

FOREIGN PATENT DOCUMENTS

| WO | 9416693 | 8/1994 |
| WO | 9420492 | 9/1994 |
| WO | 0136384 | 5/2001 |
| WO | 0144180 | 6/2001 |
| WO | 02051804 | 7/2002 |
| WO | 02083637 | 10/2002 |
| WO | 02083638 | 10/2002 |
| WO | 03004470 | 1/2003 |
| WO | 03082816 | 10/2003 |

OTHER PUBLICATIONS

Ortego, et al. 3-Hydroxy-3-methylglutaryl coenzyme A reductase inhibitors increase the binding activity and nuclear level of Oct1 in mononuclear cells. European Journal of Pharmacology (2002), vol. 448(2-3), pp. 113-121.
Roth, et al., Relationship between tissue selectivity and lipophilicity for inhibitors of HMG-CoA reductase. Journal of Medicinal Chemistry (1991), vol. 34(1), pp. 463-466.
Tesfamariam, et al., Differential effects of pravastatin, simvastatin, and atorvastatin on Ca2+ release and vascular reactivity. Journal of Cardiovascular Pharmacology (1999), vol. 34(1), pp. 95-101.
Woo, et al. Atorvastatin, an HMG-CoA reductase inhibitor and effective lipid-regulating agent. Part III. Syntheses of [2H5]-, [13C8], and [13C7, 15N]atorvastatin and their application in metabolic and pharmacokinetic studies. Journal of Labelled Compounds & Radiopharmaceuticals (1999), vol. 42(2), pp. 135-145.
Kearney, et al. The interconversion kinetics, equilibrium and solubilities of the lactone and hydroxyacid forms of the HMG-CoA reductase inhibitor, CI-981. Pharmaceutical Research (1993). vol. 10(10), pp. 1461-1465.
Chen et al., Solid-State Behavior of Cromolyn Sodium Hydrates, Journal of Pharmaceutical Sciences, vol. 88. No. 11, pp. 1191-1200, (1999).

\* cited by examiner

*Primary Examiner* — Rei-tsang Shiao
(74) *Attorney, Agent, or Firm* — Francis J. Tinney

(57) ABSTRACT

Novel salt forms of [R—(R*,R*)]-2-(4-fluorophenyl)-β,δ-dihydroxy-5-(1-methylethyl)-3-phenyl-4-[(phenylamino) carbonyl]-1H-pyrrole-1-heptanoic acid characterized by their X-ray powder diffraction pattern and solid-state NMR spectra are described, as well as methods for the preparation and pharmaceutical composition of the same, which are useful as agents for treating hyperlipidemia, hypercholesterolemia, osteoporosis, benign prostatic hyperplasia, and Alzheimer's Disease.

6 Claims, 30 Drawing Sheets

SALT FORMS OF [R-(R*,R*)]-2-(4-FLUOROPHENYL)-BETA, DELTA-DIHYDROXY-5-(1-METHYLETHYL)-3-PHENYL-4[PHENYLAMINO) CARBONYL]-1H-PYRROLE-1-HEPTANOIC ACID

This application is a divisional application of U.S. Ser. No. 13/537,432 filed Jun. 29, 2012, now pending which is a divisional application of U.S. Ser. No. 12/966,488 filed Dec. 13, 2010, now U.S. Pat. No. 8,236,966 which is a divisional application of U.S. Ser. No. 11/579,656 filed on Mar. 12, 2008, now U.S. Pat. No. 7,875,731 which is a 371 application of PCT/IB2005/001237 filed on Apr. 25, 2005, which claims benefit of provisional application U.S. Ser. No. 60/568,379 filed on May 5, 2004, all of which are incorporated herein by reference in their entirety.

FIELD OF THE INVENTION

The present invention relates to novel salt forms of atorvastatin which is known by the chemical name [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid, useful as pharmaceutical agents, to methods for their production and isolation to pharmaceutical compositions which include these compounds and a pharmaceutically acceptable carrier, as well as methods of using such compositions to treat subjects, including human subjects, suffering from hyperlipidemia, hypercholesterolemia, benign prostatic hyperplasia, osteoporosis, and Alzheimer's Disease.

BACKGROUND OF THE INVENTION

The conversion of 3-hydroxy-3-methylglutaryl-coenzyme A (HMG-CoA) to mevalonate is an early and rate-limiting step in the cholesterol biosynthetic pathway. This step is catalyzed by the enzyme HMG-CoA reductase. Statins inhibit HMG-CoA reductase from catalyzing this conversion. As such, statins are collectively potent lipid lowering agents.

Atorvastatin calcium is currently sold as Lipitor® Lipitor having the chemical name [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1) trihydrate and the formula:

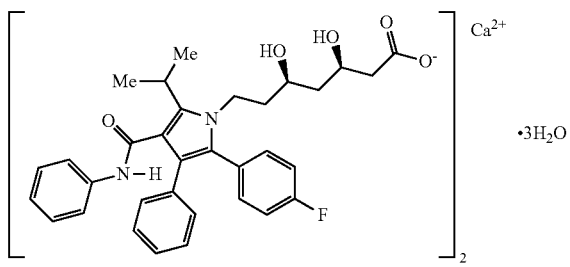

The nonproprietary name designated by USAN (United States Adopted Names) is atorvastatin calcium and by INN (International Nonproprietary Name) is atorvastatin. Under the established guiding principles of USAN, the salt is included in the name whereas under INN guidelines, a salt description is not included in the name.

Atovastatin calcium is a selective, competitive inhibitor of HMG-CoA reductase. As such, atorvastatin calcium is a potent lipid lowering compound and is thus useful as a hypolipidemic and/or hypocholesterolemic agent, as well as in the treatment of osteoporosis, benign prostatic hyperplasia, and Alzheimer's disease.

A number of patents have issued disclosing atorvastatin calcium, formulations of atorvastatin calcium, as well as processes and key intermediates for preparing atorvastatin calcium. These include: U.S. Pat. Nos. 4,681,893; 5,273,995; 5,003,080; 5,097,045; 5,103,024; 5,124,482; 5,149,837; 5,155,251; 5,216,174; 5,245,047; 5,248,793; 5,280,126; 5,397,792; 5,342,952; 5,298,627; 5,446,054; 5,470,981; 5,489,690; 5,489,691; 5,510,488; 5,686,104; 5,998,633; 6,087,511; 6,126,971; 6,433,213; and 6,476,235, which are herein incorporated by reference.

Atorvastatin calcium can exist in crystalline, liquid-crystalline, non-crystalline and amorphous forms.

Crystalline forms of atorvastatin calcium are disclosed in U.S. Pat. Nos. 5,969,156, 6,121,461, and 6,605,729 which are herein incorporated by reference.

Additionally, a number of published International Patent Applications have disclosed crystalline forms of atorvastatin calcium, as well as processes for preparing amorphous atorvastatin calcium. These include: WO 00/71116; WO 01/28999; WO 01/36384; WO 01/42209; WO 02/41834; WO 02/43667; WO 02/43732; WO 02/051804; WO 02/057228; WO 02/057229; WO 02/057274; WO 02/059087; WO 02/072073; WO 02/083637; WO 02/083638; and WO 02/089788.

Atorvastatin is prepared as its calcium salt, i.e., [R—(R*, R*)]-2-(4-fluorophenyl)-β,δ-dihydroxy-5-(1-methylethyl)-3-phenyl-4-[(phenylamino)carbonyl]-1H-pyrrole-1-1-heptanoic acid calcium salt (2:1). The calcium salt is desirable since it enables atorvastatin to be conveniently formulated in, for example, tablets, capsules, lozenges, powders, and the like for oral administration.

U.S. Pat. No. 5,273,995 discloses the mono-sodium, mono-potassium, hemi-calcium, N-methylglucamine, hemi-magnesium, hemi-zinc, and the 1-deoxy-1-(methylamino)-D-glucitol (N-methylglucamine) salts of atorvastatin.

Also, atorvastatin free acid, disclosed in U.S. Pat. No. 5,273,995, can be used to prepare these salts of atorvastatin.

Additionally, U.S. Pat. No. 6,583,295 B1 discloses a series of amine salts of HMG-CoA reductase inhibitors which are used in a process for isolation and/or purification of these HMG-CoA reductase. The tertiary butylamine and dicyclohexylamine salts of atorvastatin are disclosed.

We have now surprisingly and unexpectedly found novel salt forms of atorvastatin including salts with ammonium, benethamine, benzathine, dibenzylamine, diethylamine, L-lysine, morpholine, olamine, piperazine, and 2-amino-2-methylpropan-1-ol which have desirable properties. Additionally, we have surprisingly and unexpectedly found novel crystalline forms of atorvastatin which include salts with erbumine and sodium which have desirable properties. As such, these salt forms are pharmaceutically acceptable and can be used to prepare pharmaceutical formulations. Thus, the present invention provides basic salts of atorvastatin that are pure, have good stability, and have advantageous formulation properties compared to prior salt forms of atorvastatin.

SUMMARY OF THE INVENTION

Accordingly, a first aspect of the invention is directed to atorvastatin ammonium and hydrates thereof characterized by the following x-ray powder diffraction pattern expressed in terms of the 2θ and relative intensities with a relative intensity of >30% measured on a Bruker D5000 diffractometer with CuK$_\alpha$ radiation:

| Degree 2θ | Relative Intensity (>30%) |
|---|---|
| 3.5 | 49.0 |
| 4.4 | 34.8 |
| 7.4 | 36.5 |
| 7.8 | 58.0 |
| 8.8 | 53.9 |
| 9.3 | 44.1 |
| 9.9 | 43.8 |
| 10.6 | 80.3 |
| 12.4 | 35.1 |
| 14.1 | 30.1 |
| 16.8 | 54.5 |
| 18.3 | 56.2 |
| 19.0 | 67.8 |
| 19.5 | 100.0 |
| 20.3 | 81.4 |
| 21.4 | 69.0 |
| 21.6 | 63.8 |
| 23.1 | 65.5 |
| 23.9 | 63.8 |
| 24.8 | 69.0 |

In a second aspect, the invention is directed to Form A atorvastatin benethamine and hydrates thereof characterized by the following x-ray powder diffraction pattern expressed in terms of the 2θ and relative intensities with a relative intensity of >8% measured on a Bruker D5000 diffractometer with CuK$_\alpha$ radiation:

| Degree 2θ | Relative Intensity (>8%) |
|---|---|
| 4.7 | 42.2 |
| 5.3 | 21.7 |
| 6.0 | 12.9 |
| 7.8 | 9.6 |
| 8.9 | 53.3 |
| 9.5 | 84.4 |
| 10.5 | 10.6 |
| 12.0 | 11.5 |
| 13.8 | 12.1 |
| 14.3 | 13.3 |
| 15.6 | 20.1 |
| 16.7 | 24.6 |
| 16.9 | 19.9 |
| 17.6 | 52.7 |
| 17.8 | 53.1 |
| 18.1 | 59.7 |
| 18.8 | 100.0 |
| 19.1 | 39.1 |
| 19.9 | 42.4 |
| 21.3 | 36.2 |
| 21.9 | 22.8 |
| 22.7 | 19.8 |
| 23.6 | 52.4 |
| 24.3 | 23.5 |
| 25.9 | 23.5 |
| 26.3 | 36.2 |
| 27.0 | 13.5 |
| 27.9 | 11.8 |
| 28.8 | 9.4 |
| 29.6 | 9.8 |

In a third aspect, the invention is directed to Form A atorvastatin benethamine and hydrates thereof characterized by the following solid-state $^{13}$C nuclear magnetic resonance (SSNMR) spectrum wherein chemical shift is expressed in parts per million (ppm):

| Peak # | ppm* |
|---|---|
| 1 | 180.1 |
| 2 | 178.8 |
| 3 | 165.1 |
| 4 | 164.1 |
| 5 | 162.8 |
| 6 | 161.7 |
| 7 | 160.7 |
| 8 | 140.6 |
| 9 | 139.6 |
| 10 | 137.9 |
| 11 | 136.1 |
| 12 | 133.0 |
| 13 | 129.6 |
| 14 | 127.3 |
| 15 | 126.4 |
| 16 | 125.4 |
| 17 | 123.1 |
| 18 | 122.5 |
| 19 | 121.6 |
| 20 | 121.1 |
| 21 | 119.9 |
| 22 | 116.4 |
| 23 | 115.4 |
| 24 | 114.5 |
| 25 | 114.0 |
| 26 | 66.0 |
| 27 | 65.5 |
| 28 | 64.6 |
| 29 | 53.6 |
| 30 | 51.5 |
| 31 | 51.0 |
| 32 | 47.8 |
| 33 | 44.6 |
| 34 | 43.3 |
| 35 | 41.4 |
| 36 | 40.9 |
| 37 | 38.5 |
| 38 | 37.7 |
| 39 | 36.8 |
| 40 | 34.0 |
| 41 | 32.7 |
| 42 | 26.5 |
| 43 | 25.1 |
| 44 | 23.5 |
| 45 | 23.1 |
| 46 | 19.7 |
| 47 | 19.1 |

*Values in ppm with respect to trimethylsilane (TMS) at 0 ppm; referenced using an external sample of adamantane, setting is upfield resonance to 29.5 ppm.

In a fourth aspect, the present invention is directed to Form A atorvastatin benethamine and hydrates thereof characterized by the following solid-state $^{19}$F nuclear magnetic resonance spectrum wherein chemical shift is expressed in parts per million:

| Peak # | ppm* |
|---|---|
| 1 | −113.2 |
| 2 | −114.2 |

*Values in ppm with respect to CCl$_3$F at 0 ppm, referenced using an external standard of trifluoroacetic acid (50% V/V in water) at −76.54 ppm.

In a fifth aspect, the invention is directed to Form B atorvastatin benethamine and hydrates thereof characterized by the following x-ray powder diffraction pattern expressed in terms of the 2θ and relative intensities with a relative intensity of >6% measured on a Bruker D5000 diffractometer with CuK$_\alpha$ radiation:

| Degree 2θ | Relative Intensity (>6%) |
|---|---|
| 4.1 | 9.8 |
| 5.0 | 11.3 |
| 5.8 | 8.8 |
| 7.1 | 10.4 |
| 8.4 | 13.3 |
| 8.9 | 53.2 |
| 10.0 | 8.1 |
| 11.6 | 13.6 |
| 12.6 | 16.6 |
| 14.4 | 46.3 |
| 14.8 | 13.5 |
| 16.5 | 15.4 |
| 17.7 | 23.6 |
| 18.6 | 20.2 |
| 20.2 | 100.0 |
| 21.4 | 30.6 |
| 21.6 | 24.7 |
| 22.3 | 5.9 |
| 22.7 | 6.3 |
| 23.4 | 8.4 |
| 23.6 | 12.8 |
| 25.0 | 10.2 |
| 25.2 | 12.2 |
| 25.9 | 19.2 |
| 26.2 | 30.1 |
| 28.0 | 6.9 |
| 28.3 | 5.4 |
| 29.3 | 6.4 |
| 29.7 | 5.9 |
| 31.8 | 5.3 |
| 33.5 | 12.1 |
| 35.2 | 6.6 |
| 35.8 | 5.9 |

In a sixth aspect, the invention is directed to Form B atorvastatin benethamine and hydrates thereof characterized by the following solid-state $^{13}C$ nuclear magnetic resonance spectrum wherein chemical shift is expressed in parts per million:

| Peak # | ppm* |
|---|---|
| 1 | 179.4 |
| 2 | 165.6 |
| 3 | 162.4 |
| 4 | 140.1 |
| 5 | 138.6 |
| 6 | 133.6 |
| 7 | 132.8 |
| 8 | 129.9 |
| 9 | 128.2 |
| 10 | 125.7 |
| 11 | 123.6 |
| 12 | 114.8 |
| 13 | 69.6 |
| 14 | 69.0 |
| 15 | 52.3 |
| 16 | 49.8 |
| 17 | 43.1 |
| 18 | 42.2 |
| 19 | 39.6 |
| 20 | 38.9 |
| 21 | 31.5 |
| 22 | 26.5 |
| 23 | 23.5 |
| 24 | 19.6 |

*Values in ppm with respect to trimethylsilane (TMS) at 0 ppm; referenced using an external sample of adamantane, setting is upfield resonance to 29.5 ppm.

In a seventh aspect, the invention is directed to Form B atorvastatin benethamine and hydrates thereof characterized by the following solid-state $^{19}F$ nuclear magnetic resonance spectrum wherein chemical shift is expressed in parts per million:

| Peak # | ppm* |
|---|---|
| 1 | −113.7 |
| 2 | −114.4 |

*Values in ppm with respect to $CCl_3F$ at 0 ppm, referenced using an external standard of trifluoroacetic acid (50% V/V in water) at −76.54 ppm.

In a eighth aspect, the invention is directed to Form A atorvastatin benzathine and hydrates thereof characterized by the following x-ray powder diffraction pattern expressed in terms of the 2θ and relative intensities with a relative intensity of >12% measured on a Bruker D5000 diffractometer with $CuK_\alpha$ radiation:

| Degree 2θ | Relative Intensity (>12%) |
|---|---|
| 9.1 | 97.5 |
| 14.0 | 40.3 |
| 15.1 | 13.8 |
| 15.5 | 13.7 |
| 16.1 | 15.3 |
| 16.4 | 16.8 |
| 18.2 | 40.0 |
| 19.1 | 58.5 |
| 19.6 | 18.1 |
| 20.5 | 100.0 |
| 21.3 | 66.3 |
| 22.1 | 15.5 |
| 22.5 | 21.7 |
| 23.0 | 43.8 |
| 25.2 | 18.8 |
| 25.9 | 12.9 |
| 26.1 | 15.6 |
| 26.5 | 14.4 |
| 28.0 | 14.2 |
| 28.6 | 17.1 |

In a ninth aspect, the invention is directed to Form B atorvastatin benzathine and hydrates thereof characterized by the following x-ray powder diffraction pattern expressed in terms of the 2θ and relative intensities with a relative intensity of >9% measured on a Bruker D5000 diffractometer with $CuK_\alpha$ radiation:

| Degree 2θ | Relative Intensity (>9%) |
|---|---|
| 8.3 | 100.0 |
| 9.1 | 9.4 |
| 10.2 | 62.6 |
| 11.7 | 9.1 |
| 13.2 | 10.2 |
| 14.4 | 21.1 |
| 15.8 | 18.1 |
| 16.6 | 20.0 |
| 17.1 | 14.8 |
| 18.6 | 34.0 |
| 19.1 | 40.7 |
| 19.4 | 23.0 |
| 19.7 | 14.8 |
| 20.6 | 24.0 |
| 20.9 | 13.1 |
| 21.4 | 28.8 |
| 21.8 | 29.3 |
| 22.3 | 24.9 |
| 22.6 | 29.2 |
| 23.3 | 46.1 |
| 23.5 | 31.3 |
| 24.3 | 11.0 |
| 25.0 | 18.9 |
| 26.5 | 14.8 |

-continued

| Degree 2θ | Relative Intensity (>9%) |
|---|---|
| 26.8 | 11.6 |
| 27.4 | 13.2 |
| 27.9 | 12.3 |
| 28.2 | 9.3 |
| 28.9 | 9.3 |
| 29.1 | 9.8 |
| 29.7 | 10.9 |

In a tenth aspect, the invention is directed to Form C atorvastatin benzathine and hydrates thereof characterized by the following x-ray powder diffraction pattern expressed in terms of the 2θ and relative intensities with a relative intensity of >13% measured on a Bruker D5000 diffractometer with CuK$_\alpha$ radiation:

| Degree 2θ | Relative Intensity (>13%) |
|---|---|
| 3.9 | 59.5 |
| 6.9 | 23.3 |
| 7.9 | 30.5 |
| 9.7 | 70.6 |
| 11.9 | 100.0 |
| 12.8 | 17.8 |
| 13.2 | 41.4 |
| 15.5 | 15.3 |
| 16.3 | 13.1 |
| 16.8 | 17.4 |
| 17.2 | 39.5 |
| 18.9 | 18.4 |
| 19.5 | 31.5 |
| 19.9 | 31.7 |
| 20.4 | 58.2 |
| 20.7 | 43.9 |
| 21.4 | 29.2 |
| 23.0 | 19.0 |
| 23.4 | 18.7 |
| 24.0 | 26.6 |
| 24.3 | 33.6 |
| 24.6 | 41.4 |
| 25.9 | 21.5 |
| 26.2 | 28.4 |

In an eleventh aspect, the invention is directed to atorvastatin dibenzylamine and hydrates thereof characterized by the following x-ray powder diffraction pattern expressed in terms of the 2θ and relative intensities with a relative intensity of >8% measured on a Bruker D5000 diffractometer with CuK$_\alpha$ radiation:

| Degree 2θ | Relative Intensity (>8%) |
|---|---|
| 4.6 | 10.6 |
| 8.3 | 50.8 |
| 9.6 | 13.8 |
| 9.8 | 10.0 |
| 10.3 | 14.9 |
| 10.4 | 12.1 |
| 10.6 | 19.8 |
| 11.8 | 13.9 |
| 12.4 | 7.7 |
| 13.3 | 10.0 |
| 14.5 | 10.2 |
| 14.9 | 11.6 |
| 15.9 | 11.8 |

-continued

| Degree 2θ | Relative Intensity (>8%) |
|---|---|
| 16.7 | 10.4 |
| 17.4 | 23.6 |
| 18.4 | 19.7 |
| 18.7 | 38.5 |
| 19.4 | 24.2 |
| 19.8 | 48.0 |
| 20.7 | 100.0 |
| 21.3 | 56.4 |
| 21.6 | 26.7 |
| 22.1 | 13.4 |
| 22.5 | 21.9 |
| 23.0 | 9.7 |
| 23.4 | 29.5 |
| 23.7 | 29.7 |
| 24.3 | 11.0 |
| 24.6 | 13.6 |
| 25.1 | 13.0 |
| 25.8 | 31.9 |
| 26.7 | 8.5 |
| 28.0 | 10.8 |
| 29.2 | 12.2 |
| 33.4 | 9.8 |
| 34.6 | 8.1 |
| 34.8 | 9.1 |

In a twelfth aspect, the invention is directed to atorvastatin dibenzylamine and hydrates thereof characterized by the following solid-state $^{13}$C nuclear magnetic resonance spectrum wherein chemical shift is expressed in parts per million:

| Peak # | ppm* |
|---|---|
| 1 | 179.1 |
| 2 | 166.2 |
| 3 | 163.1 |
| 4 | 160.8 |
| 5 | 140.6 |
| 6 | 135.2 |
| 7 | 134.3 |
| 8 | 133.4 |
| 9 | 131.9 |
| 10 | 131.1 |
| 11 | 129.4 |
| 12 | 128.3 |
| 13 | 125.6 |
| 14 | 124.2 |
| 15 | 122.9 |
| 16 | 119.7 |
| 17 | 115.4 |
| 18 | 69.7 |
| 19 | 68.6 |
| 20 | 52.6 |
| 21 | 51.3 |
| 22 | 43.0 |
| 23 | 41.9 |
| 24 | 38.8 |
| 25 | 38.2 |
| 26 | 26.7 |
| 27 | 23.3 |
| 28 | 20.0 |

*Values in ppm with respect to trimethylsilane (TMS) at 0 ppm; referenced using an external sample of adamantane, setting is upfield resonance to 29.5 ppm.

In a thirteenth aspect, the invention is directed to atorvastatin dibenzylamine and hydrates thereof characterized by the following solid-state $^{19}$F nuclear magnetic resonance spectrum wherein chemical shift is expressed in parts per million:

| Peak # | ppm* |
|---|---|
| 1 | −107.8 |

*Values in ppm with respect to CCl$_3$F at 0 ppm, referenced using an external standard of trifluoroacetic acid (50% V/V in water) at −76.54 ppm.

In a fourteenth aspect, the invention is directed to Form A atorvastatin diethylamine and hydrates thereof characterized by the following x-ray powder diffraction pattern expressed in terms of the 2θ and relative intensities with a relative intensity of >20% measured on a Bruker D5000 diffractometer with CuK$_\alpha$ radiation:

| Degree 2θ | Relative Intensity (>20%) |
|---|---|
| 7.0 | 53.0 |
| 8.2 | 32.0 |
| 10.8 | 59.3 |
| 12.3 | 36.0 |
| 13.3 | 60.8 |
| 14.4 | 56.0 |
| 16.1 | 35.5 |
| 16.5 | 39.3 |
| 17.0 | 40.0 |
| 18.2 | 49.3 |
| 18.4 | 100.0 |
| 19.4 | 23.0 |
| 20.0 | 20.5 |
| 21.0 | 54.5 |
| 21.7 | 24.5 |
| 22.3 | 30.5 |
| 23.0 | 68.8 |
| 24.3 | 25.5 |
| 25.1 | 38.5 |
| 25.4 | 26.9 |
| 26.3 | 41.3 |
| 26.8 | 21.8 |
| 28.4 | 23.8 |

In an fifteenth aspect, the invention is directed to Form B atorvastatin diethylamine and hydrates thereof characterized by the following x-ray powder diffraction pattern expressed in terms of the 2θ and relative intensities with a relative intensity of >8% measured on a Bruker D5000 diffractometer with CuK$_\alpha$ radiation:

| Degree 2θ | Relative Intensity (>8%) |
|---|---|
| 6.1 | 8.3 |
| 7.0 | 10.6 |
| 8.3 | 26.0 |
| 10.8 | 8.5 |
| 11.5 | 21.4 |
| 12.2 | 28.2 |
| 12.5 | 12.7 |
| 13.4 | 16.5 |
| 14.5 | 10.0 |
| 15.3 | 34.2 |
| 16.1 | 17.1 |
| 16.6 | 12.8 |
| 16.8 | 16.6 |
| 17.4 | 17.3 |
| 17.9 | 8.1 |
| 18.4 | 12.8 |
| 18.7 | 8.5 |
| 19.3 | 52.2 |
| 20.5 | 21.4 |
| 21.0 | 100.0 |
| 22.3 | 13.0 |
| 23.2 | 34.2 |
| 24.6 | 23.7 |
| 25.4 | 8.2 |
| 25.9 | 8.1 |
| 26.4 | 16.9 |
| 27.6 | 25.6 |
| 29.2 | 10.6 |
| 31.2 | 8.5 |
| 32.8 | 9.1 |

In an sixteenth aspect, the invention is directed to atorvastatin erbumine and hydrates thereof characterized by the following x-ray powder diffraction pattern expressed in terms of the 2θ and relative intensities with a relative intensity of >6% measured on a Bruker D5000 diffractometer with CuK$_\alpha$ radiation:

| Degree 2θ | Relative Intensity (>6%) |
|---|---|
| 5.4 | 11.9 |
| 7.3 | 12.0 |
| 9.5 | 100.0 |
| 12.6 | 14.3 |
| 15.2 | 15.6 |
| 16.6 | 13.7 |
| 17.8 | 21.0 |
| 18.6 | 20.2 |
| 19.2 | 77.6 |
| 20.0 | 28.3 |
| 20.4 | 8.2 |
| 20.9 | 22.3 |
| 21.6 | 14.3 |
| 22.2 | 26.6 |
| 22.4 | 13.3 |
| 22.6 | 14.5 |
| 23.7 | 8.7 |
| 24.2 | 31.6 |
| 25.0 | 15.5 |
| 26.5 | 12.3 |
| 28.2 | 7.9 |
| 29.5 | 6.3 |
| 30.6 | 6.5 |

In a seventeenth aspect, the invention is directed to atorvastatin erbumine and hydrates thereof characterized by the following solid-state $^{13}$C nuclear magnetic resonance spectrum wherein chemical shift is expressed in parts per million:

| Peak # | ppm* |
|---|---|
| 1 | 179.3 |
| 2 | 164.5 |
| 3 | 163.0 |
| 4 | 160.9 |
| 5 | 141.3 |
| 6 | 140.9 |
| 7 | 135.3 |
| 8 | 134.5 |
| 9 | 132.8 |
| 10 | 129.0 |
| 11 | 127.7 |
| 12 | 124.5 |
| 13 | 121.8 |
| 14 | 120.2 |
| 15 | 116.5 |
| 16 | 115.5 |
| 17 | 112.4 |

| Peak # | ppm* |
|---|---|
| 18 | 71.3 |
| 19 | 50.3 |
| 20 | 47.7 |
| 21 | 42.6 |
| 22 | 41.0 |
| 23 | 28.5 |
| 24 | 26.4 |
| 25 | 22.6 |
| 26 | 21.6 |

*Values in ppm with respect to trimethylsilane (TMS) at 0 ppm; referenced using an external sample of adamantane, setting is upfield resonance to 29.5 ppm.

In a eighteenth aspect, the invention is directed to atorvastatin erbumine and hydrates thereof characterized by the following solid-state $^{19}F$ nuclear magnetic resonance spectrum wherein chemical shift is expressed in parts per million:

| Peak # | ppm* |
|---|---|
| 1 | −110.4 |

*Values in ppm with respect to $CCl_3F$ at 0 ppm, referenced using an external standard of trifluoroacetic acid (50% V/V in water) at −76.54 ppm.

In a nineteenth aspect, the invention is directed to atorvastatin L-lysine and hydrates thereof characterized by the following x-ray powder diffraction pattern expressed in terms of the 2θ and relative intensities with a relative intensity of >40% measured on a Bruker D5000 diffractometer with $CuK_\alpha$ radiation:

| Degree 2θ | Relative Intensity (>40%) |
|---|---|
| 6.7 | 100.0 |
| 9.5 | 62.1 |
| 9.8 | 74.3 |
| 17.1 | 80.4 |
| 18.7 | 86.5 |
| 19.6 | 76.8 |
| 21.1 | 77.1 |
| 22.1 | 72.1 |
| 22.5 | 77.9 |
| 24.0 | 59.5 |

In a twentieth aspect, the invention is directed to atorvastatin morpholine and hydrates thereof characterized by the following x-ray powder diffraction pattern expressed in terms of the 2θ and relative intensities with a relative intensity of >9% measured on a Bruker D5000 diffractometer with $CuK_\alpha$ radiation:

| Degree 2θ | Relative Intensity (>9%) |
|---|---|
| 4.8 | 15.9 |
| 5.7 | 10.7 |
| 6.4 | 11.6 |
| 8.6 | 9.2 |
| 9.7 | 52.5 |
| 12.8 | 6.8 |
| 14.1 | 10.3 |
| 14.6 | 22.5 |
| 16.0 | 42.1 |
| 16.3 | 26.7 |
| 16.5 | 21.3 |
| 17.3 | 19.6 |
| 17.5 | 29.3 |
| 18.1 | 16.5 |
| 18.9 | 46.1 |
| 19.2 | 27.3 |
| 19.6 | 85.9 |
| 19.9 | 19.8 |
| 20.8 | 42.2 |
| 21.2 | 16.9 |
| 22.1 | 89.9 |
| 23.1 | 19.6 |
| 23.9 | 100.0 |
| 24.6 | 26.0 |
| 25.0 | 39.0 |
| 25.7 | 11.0 |
| 27.0 | 14.1 |
| 28.1 | 10.1 |
| 28.5 | 25.8 |
| 29.6 | 11.8 |
| 30.1 | 9.9 |
| 30.9 | 13.4 |
| 31.0 | 14.1 |
| 32.0 | 13.0 |
| 32.4 | 16.5 |
| 33.4 | 14.1 |
| 33.9 | 11.0 |
| 34.6 | 18.0 |
| 35.4 | 14.3 |
| 36.8 | 18.2 |
| 37.6 | 11.4 |

In a twenty-first aspect, the invention is directed to atorvastatin morpholine and hydrates thereof characterized by the following solid-state $^{13}C$ nuclear magnetic resonance spectrum wherein chemical shift is expressed in parts per million:

| Peak # | ppm* |
|---|---|
| 1 | 179.3 |
| 2 | 165.9 |
| 3 | 162.7 |
| 4 | 160.5 |
| 5 | 139.6 |
| 6 | 137.8 |
| 7 | 134.3 |
| 8 | 131.2 |
| 9 | 129.6 |
| 10 | 128.7 |
| 11 | 127.4 |
| 12 | 122.9 |
| 13 | 120.8 |
| 14 | 117.9 |
| 15 | 116.3 |
| 16 | 70.8 |
| 17 | 69.5 |
| 18 | 63.4 |
| 19 | 42.4 |
| 20 | 41.2 |
| 21 | 40.5 |
| 22 | 24.8 |
| 23 | 20.6 |

*Values in ppm with respect to trimethylsilane (TMS) at 0 ppm; referenced using an external sample of adamantane, setting is upfield resonance to 29.5 ppm.

In a twenty-second aspect, the invention is directed to atorvastatin morpholine and hydrates thereof characterized by the following $^{19}F$ nuclear magnetic resonance spectrum wherein chemical shift is expressed in parts per million:

| Peak # | ppm* |
|---|---|
| 1 | −117.6 |

*Values in ppm with respect to CCl$_3$F at 0 ppm, referenced using an external standard of trifluoroacetic acid (50% V/V in water) at −76.54 ppm.

In a twenty-third aspect, the invention is directed to atorvastatin olamine and hydrates thereof characterized by the following x-ray powder diffraction pattern expressed in terms of the 2θ and relative intensities with a relative intensity of >15% measured on a Bruker D5000 diffractometer with CuK$_\alpha$ radiation:

| Degree 2θ | Relative Intensity (>15%) |
|---|---|
| 8.5 | 100.0 |
| 9.8 | 74.7 |
| 11.4 | 17.3 |
| 12.0 | 15.6 |
| 16.3 | 27.7 |
| 17.4 | 43.9 |
| 18.6 | 85.5 |
| 19.6 | 45.8 |
| 20.1 | 43.9 |
| 20.9 | 96.0 |
| 21.4 | 31.6 |
| 22.0 | 30.5 |
| 22.5 | 66.1 |
| 22.8 | 35.6 |
| 23.5 | 20.5 |
| 24.1 | 42.7 |
| 25.1 | 23.3 |
| 25.9 | 25.0 |
| 26.2 | 33.1 |
| 27.8 | 19.3 |
| 28.8 | 27.5 |
| 29.6 | 20.0 |
| 31.7 | 20.5 |
| 37.7 | 22.5 |

In a twenty-fourth aspect, the invention is directed to atorvastatin olamine and hydrates thereof characterized by the following $^{13}$C nuclear magnetic resonance spectrum wherein chemical shift is expressed in parts per million:

| Peak # | ppm* |
|---|---|
| 1 | 182.0 |
| 2 | 178.9 |
| 3 | 165.4 |
| 4 | 161.6 |
| 5 | 159.5 |
| 6 | 137.4 |
| 7 | 134.8 |
| 8 | 133.8 |
| 9 | 131.0 |
| 10 | 128.7 |
| 11 | 128.0 |
| 12 | 127.0 |
| 13 | 123.1 |
| 14 | 122.6 |
| 15 | 121.9 |
| 16 | 120.9 |
| 17 | 120.1 |
| 18 | 117.3 |
| 19 | 115.6 |
| 20 | 114.3 |
| 21 | 66.5 |
| 22 | 66.0 |
| 23 | 65.2 |
| 24 | 58.5 |
| 25 | 58.2 |
| 26 | 51.1 |
| 27 | 47.8 |
| 28 | 46.0 |
| 29 | 43.9 |
| 30 | 42.4 |
| 31 | 41.3 |
| 32 | 40.6 |
| 33 | 39.8 |
| 34 | 25.7 |
| 35 | 23.1 |
| 36 | 21.1 |
| 37 | 20.7 |

*Values in ppm with respect to trimethylsilane (TMS) at 0 ppm; referenced using an external sample of adamantane, setting is upfield resonance to 29.5 ppm.

In a twenty-fifth aspect, the invention is directed to atorvastatin olamine and hydrates thereof characterized by the following $^{19}$F nuclear magnetic resonance spectrum wherein chemical shift is expressed in parts per million:

| Peak # | ppm* |
|---|---|
| 1 | −118.7 |

*Values in ppm with respect to CCl$_3$F at 0 ppm, referenced using an external standard of trifluoroacetic acid (50% V/V in water) at −76.54 ppm.

In a twenty-sixth aspect, the invention is directed to atorvastatin piperazine and hydrates thereof characterized by the following x-ray powder diffraction pattern expressed in terms of the 2θ and relative intensities with a relative intensity of >20% measured on a Bruker D5000 diffractometer with CuK$_\alpha$ radiation:

| Degree 2θ | Relative Intensity (>20%) |
|---|---|
| 4.4 | 20.4 |
| 7.8 | 25.5 |
| 9.3 | 27.2 |
| 11.8 | 29.7 |
| 13.2 | 22.9 |
| 16.1 | 30.0 |
| 17.7 | 30.9 |
| 19.7 | 100.0 |
| 20.4 | 55.0 |
| 22.2 | 31.9 |
| 22.9 | 36.2 |
| 23.8 | 30.7 |
| 26.4 | 32.6 |

In a twenty-seventh aspect, the invention is directed to atorvastatin sodium and hydrates thereof characterized by the following x-ray powder diffraction pattern expressed in terms of the 2θ and relative intensities with a relative intensity of >25% measured on a Bruker D5000 diffractometer with CuK$_\alpha$ radiation:

| Degree 2θ | Relative Intensity (>25%) |
|---|---|
| 3.4 | 57.8 |
| 4.1 | 29.2 |
| 4.9 | 53.0 |
| 5.6 | 32.4 |
| 6.8 | 25.2 |
| 7.6 | 68.5 |

-continued

| Degree 2θ | Relative Intensity (>25%) |
|---|---|
| 8.0 | 75.7 |
| 8.5 | 42.0 |
| 9.9 | 66.1 |
| 10.4 | 51.5 |
| 12.8 | 25.5 |
| 18.9 | 100.0 |
| 19.7 | 64.5 |
| 21.2 | 32.8 |
| 22.1 | 33.3 |
| 22.9 | 45.4 |
| 23.3 | 43.6 |
| 24.0 | 42.7 |
| 25.2 | 26.1 |

In a twenty-eighth aspect, the invention is directed to atorvastatin 2-amino-2-methylpropan-1-ol and hydrates thereof characterized by the following x-ray powder diffraction pattern expressed in terms of the 2θ and relative intensities with a relative intensity of >20% measured on a Bruker D5000 diffractometer with CuK$_\alpha$ radiation:

| Degree 2θ | Relative Intensity (>20%) |
|---|---|
| 4.2 | 95.2 |
| 6.0 | 59.9 |
| 6.2 | 43.7 |
| 8.3 | 26.3 |
| 11.5 | 20.9 |
| 12.5 | 36.5 |
| 12.6 | 31.1 |
| 16.0 | 44.4 |
| 17.5 | 54.3 |
| 18.3 | 52.8 |
| 18.8 | 34.0 |
| 19.4 | 55.3 |
| 19.7 | 100.0 |
| 21.3 | 26.7 |
| 22.0 | 31.3 |
| 22.8 | 21.7 |
| 23.4 | 29.7 |
| 23.8 | 28.6 |

In a twenty-ninth aspect, the invention is directed to atorvastatin 2-amino-2-methylpropan-1-ol and hydrates thereof characterized by the following $^{13}$C nuclear magnetic resonance spectrum wherein chemical shift is expressed in parts per million:

| Peak # | ppm* |
|---|---|
| 1 | 179.8 |
| 2 | 166.3 |
| 3 | 163.3 |
| 4 | 161.5 |
| 5 | 161.2 |
| 6 | 140.5 |
| 7 | 139.5 |
| 8 | 134.4 |
| 9 | 132.3 |
| 10 | 131.6 |
| 11 | 129.8 |
| 12 | 128.1 |
| 13 | 126.1 |
| 14 | 125.1 |
| 15 | 122.2 |
| 16 | 120.7 |
| 17 | 116.4 |
| 18 | 114.0 |
| 19 | 113.4 |
| 20 | 72.6 |
| 21 | 71.4 |
| 22 | 67.6 |
| 23 | 66.3 |
| 24 | 64.7 |
| 25 | 64.4 |
| 26 | 53.1 |
| 27 | 46.9 |
| 28 | 43.9 |
| 29 | 43.5 |
| 30 | 42.7 |
| 31 | 39.7 |
| 32 | 36.1 |
| 33 | 26.8 |
| 34 | 26.3 |
| 35 | 24.3 |
| 36 | 23.8 |
| 37 | 23.1 |
| 38 | 22.0 |
| 39 | 20.4 |

*Values in ppm with respect to trimethylsilane (TMS) at 0 ppm; referenced using an external sample of adamantane, setting is upfield resonance to 29.5 ppm.

In a thirtieth aspect, the invention is directed to atorvastatin 2-amino-2-methylpropan-1-ol and hydrates thereof characterized by the following $^{19}$F nuclear magnetic resonance spectrum wherein chemical shift is expressed in parts per million:

| Peak # | ppm* |
|---|---|
| 1 | −113.6 |
| 2 | −116.5 |

*Values in ppm with respect to CCl$_3$F at 0 ppm, referenced using an external standard of trifluoroacetic acid (50% V/V in water) at −76.54 ppm.

As inhibitors of HMG-CoA reductase, the novel salt forms of atorvastatin are useful as hypolipidemic and hypocholesterolemic agents, as well as agents in the treatment of osteoporosis, benign prostatic hyperplasia, and Alzheimer's Disease.

A still further embodiment of the present invention is a pharmaceutical composition for administering an effective amount of an atorvastatin salt in unit dosage form in the treatment methods mentioned above. Finally, the present invention is directed to methods for production of salt forms of atorvastatin.

BRIEF DESCRIPTION OF THE DRAWINGS

The invention is further described by the following non-limiting examples which refer to the accompanying FIGS. 1 to 30, short particulars of which are given below.

DETAILED DESCRIPTION OF THE INVENTION

Figure 1:
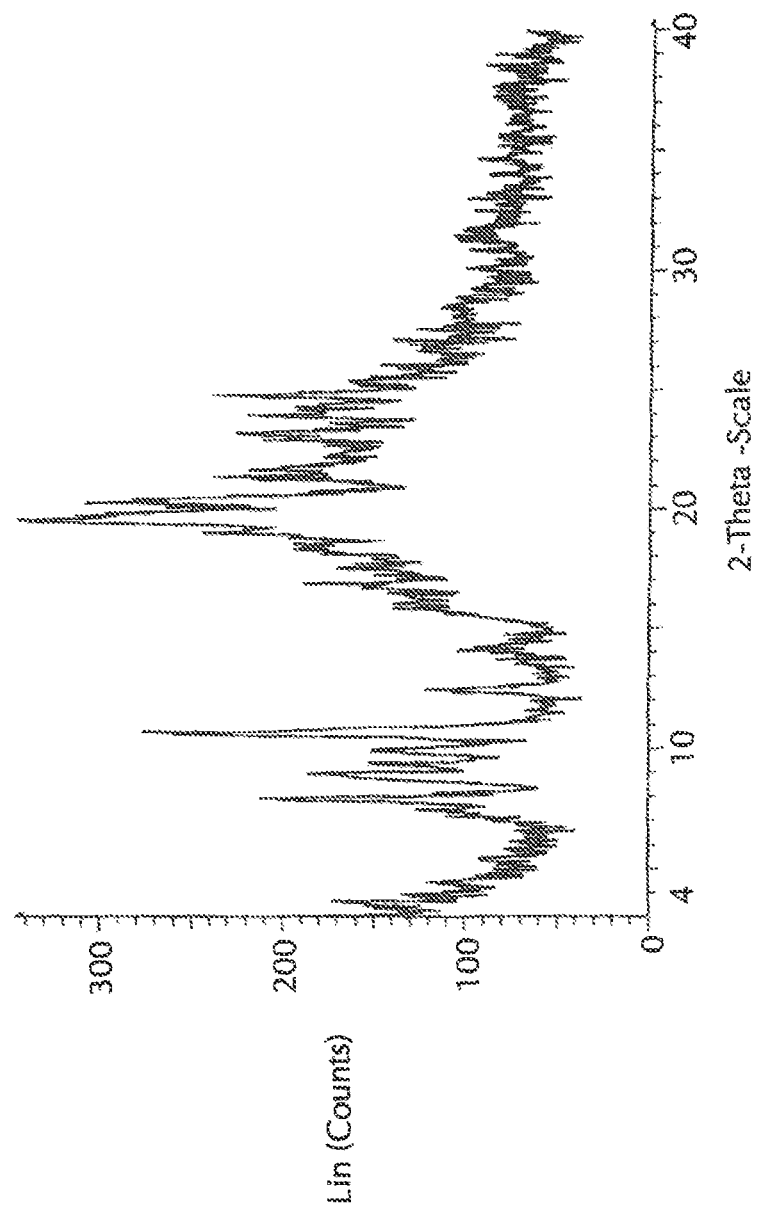
FIG. 1 Diffractogram of atorvastatin ammonium carried out on a Bruker D5000 diffractometer.
Figure 2:
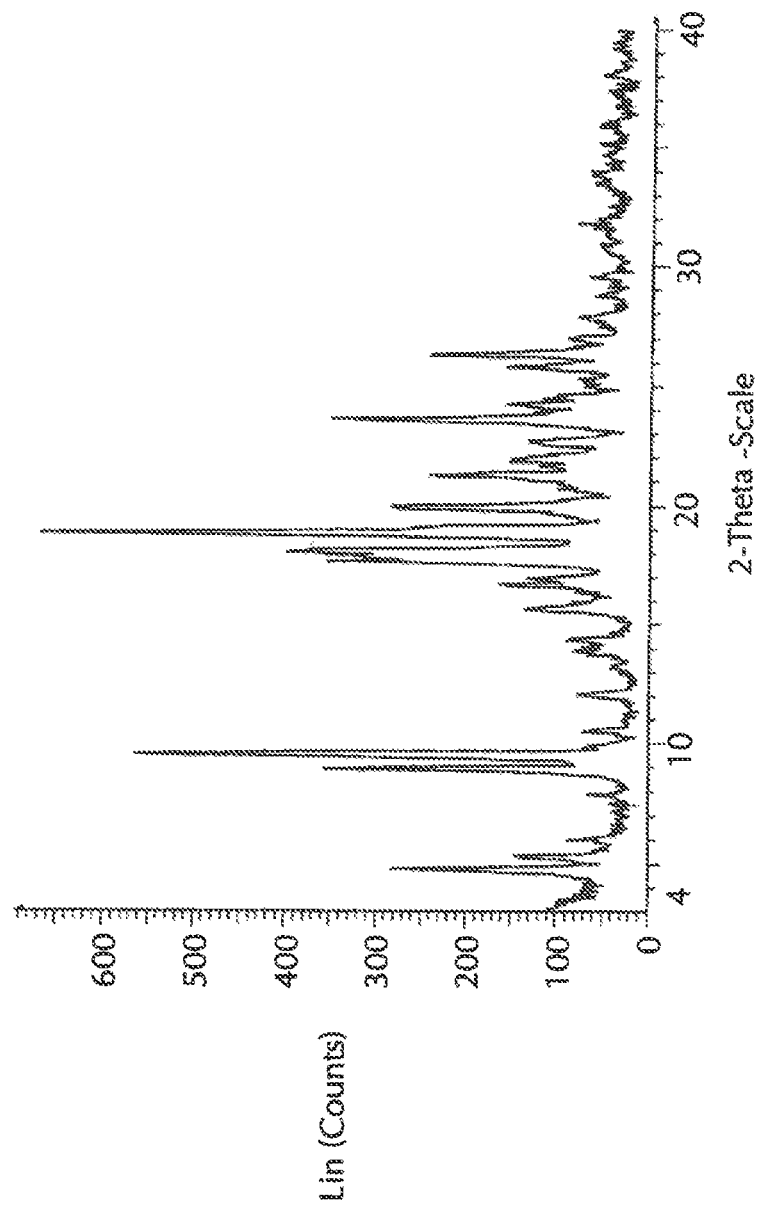
FIG. 2 Diffractogram of Form A atorvastatin benethamine carried out on a Bruker D5000 diffractometer.
Figure 3:
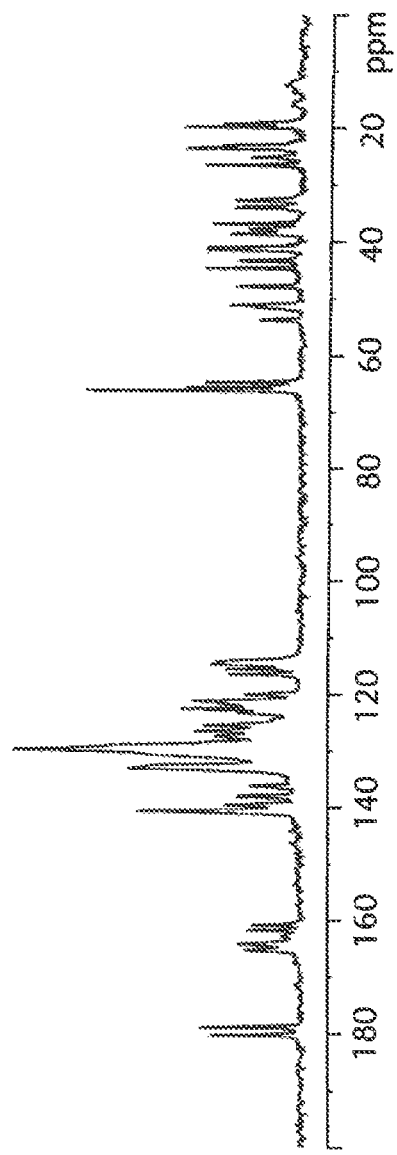
FIG. 3 Solid-state $^{13}$C nuclear magnetic resonance spectrum of Form A atorvastatin benethamine.
Figure 4:
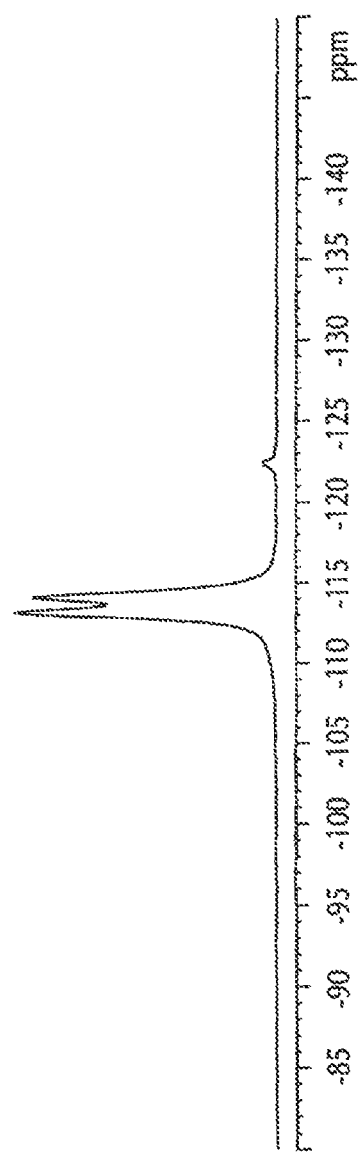
FIG. 4 Solid-state $^{19}$F nuclear magnetic resonance spectrum of Form A atorvastatin benethamine.
Figure 5:
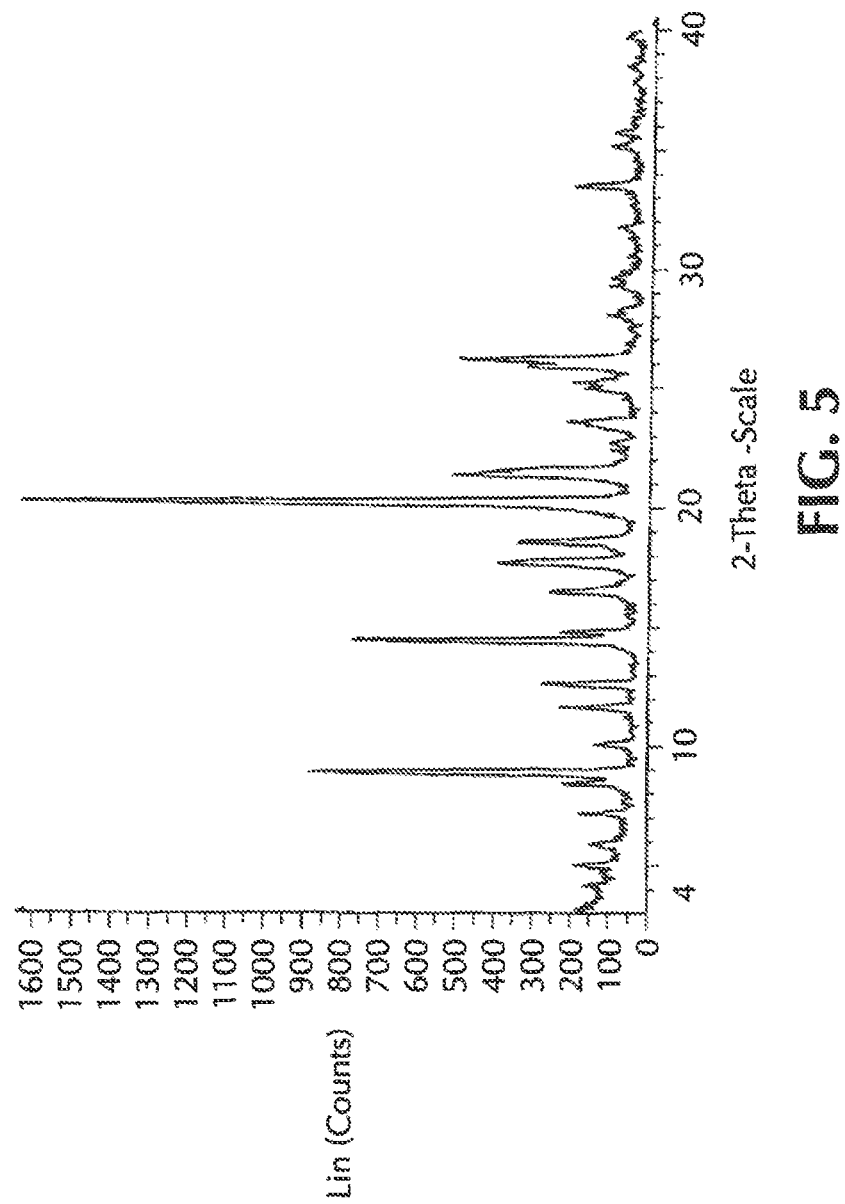
FIG. 5 Diffractogram of Form B atorvastatin benethamine carried out on a Bruker D5000 diffractometer.
Figure 6:
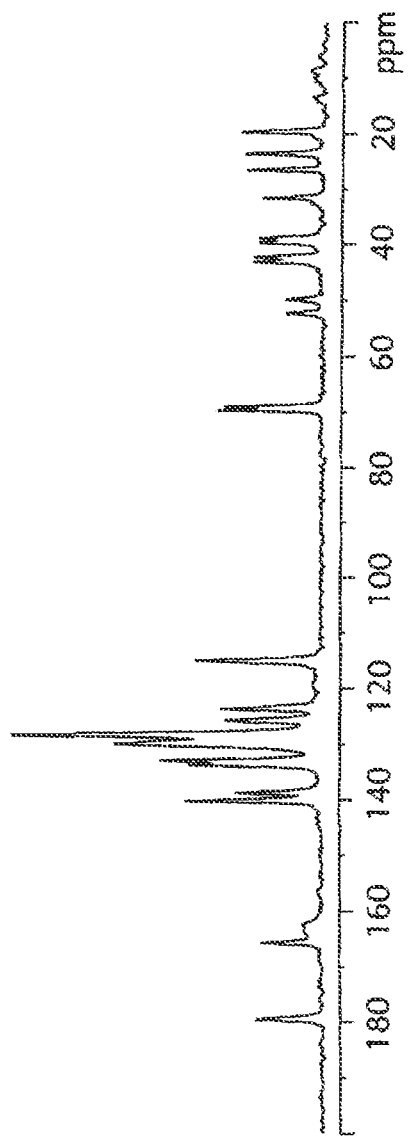
FIG. 6 Solid-state $^{13}$C nuclear magnetic resonance spectrum of Form B atorvastatin benethamine.
Figure 7:
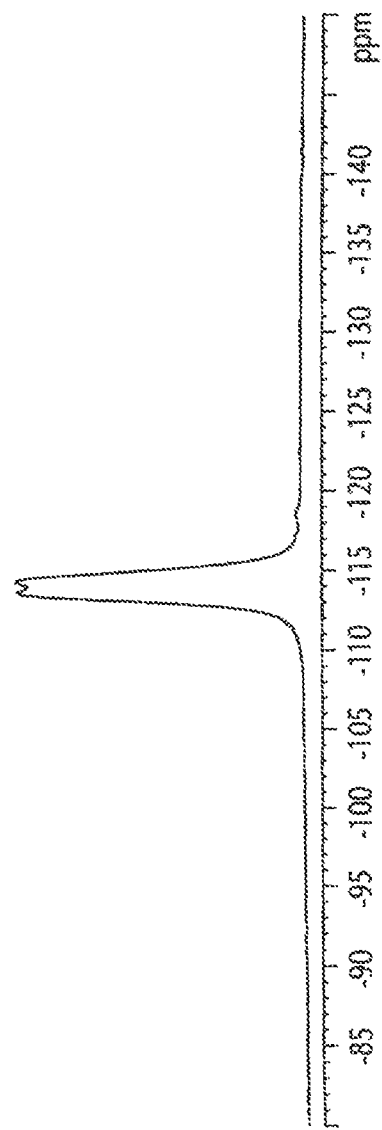
FIG. 7 Solid-state $^{19}$F nuclear magnetic resonance spectrum of Form B atorvastatin benethamine.
Figure 8:
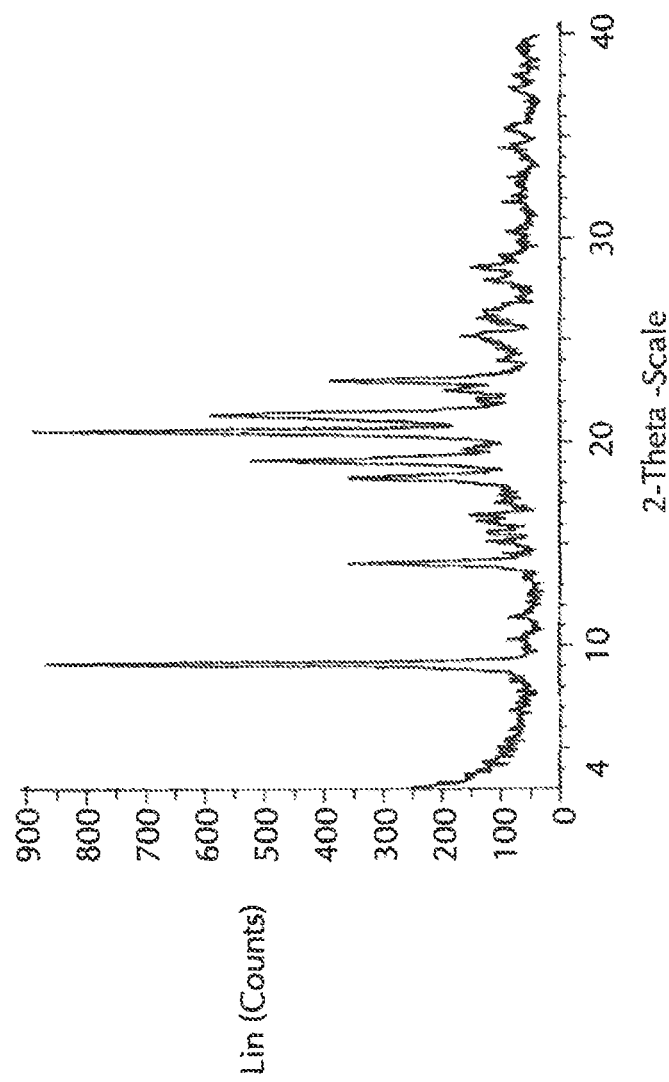
FIG. 8 Diffractogram of Form A atorvastatin benzathine carried out on a Bruker D5000 diffractometer.
Figure 9:
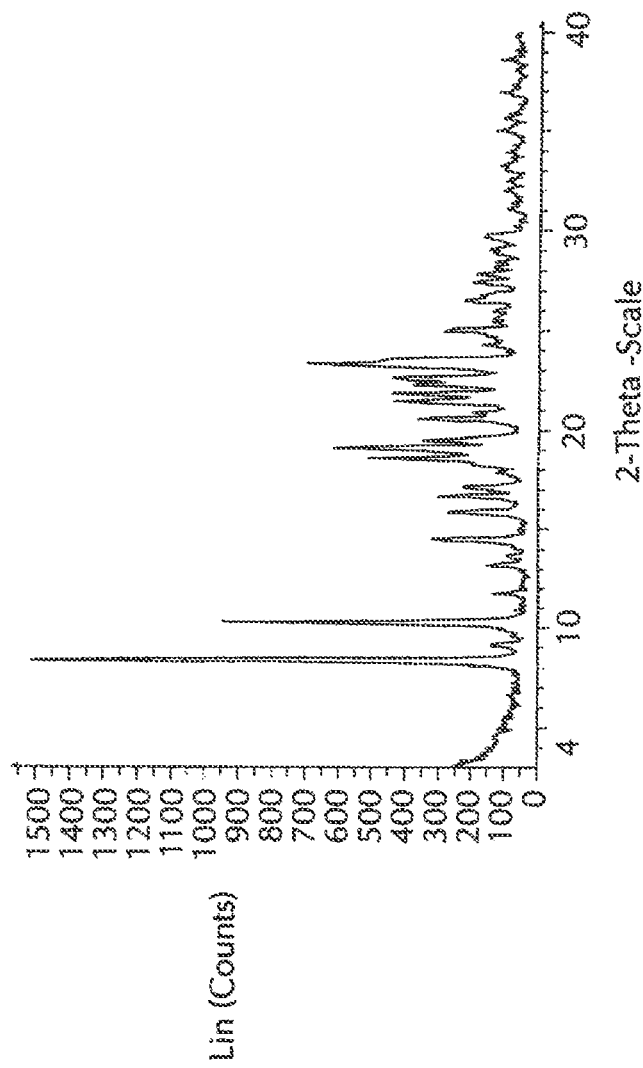
FIG. 9 Diffractogram of Form B atorvastatin benzathine carried out on a Bruker D5000 diffractometer.
Figure 10:
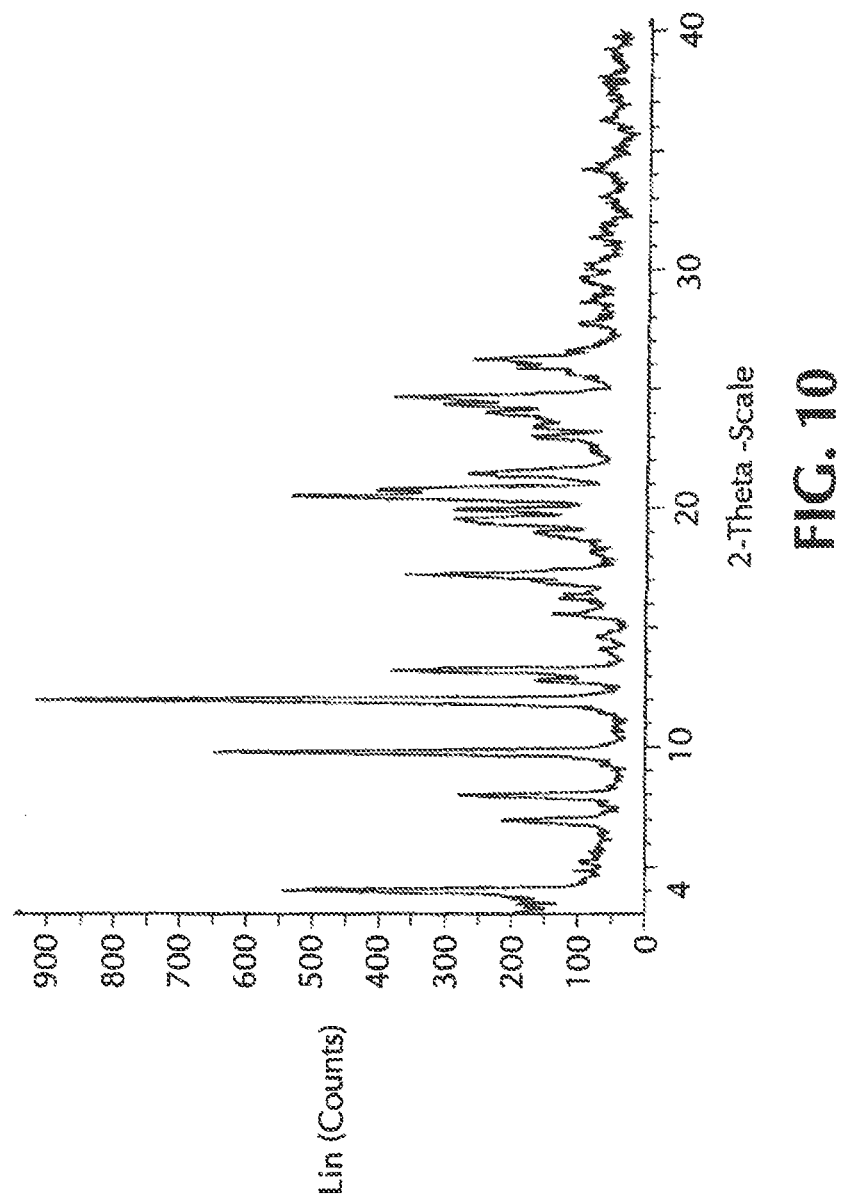
FIG. 10 Diffractogram of Form C atorvastatin benzathine carried out on a Bruker D5000 diffractometer.
Figure 11:
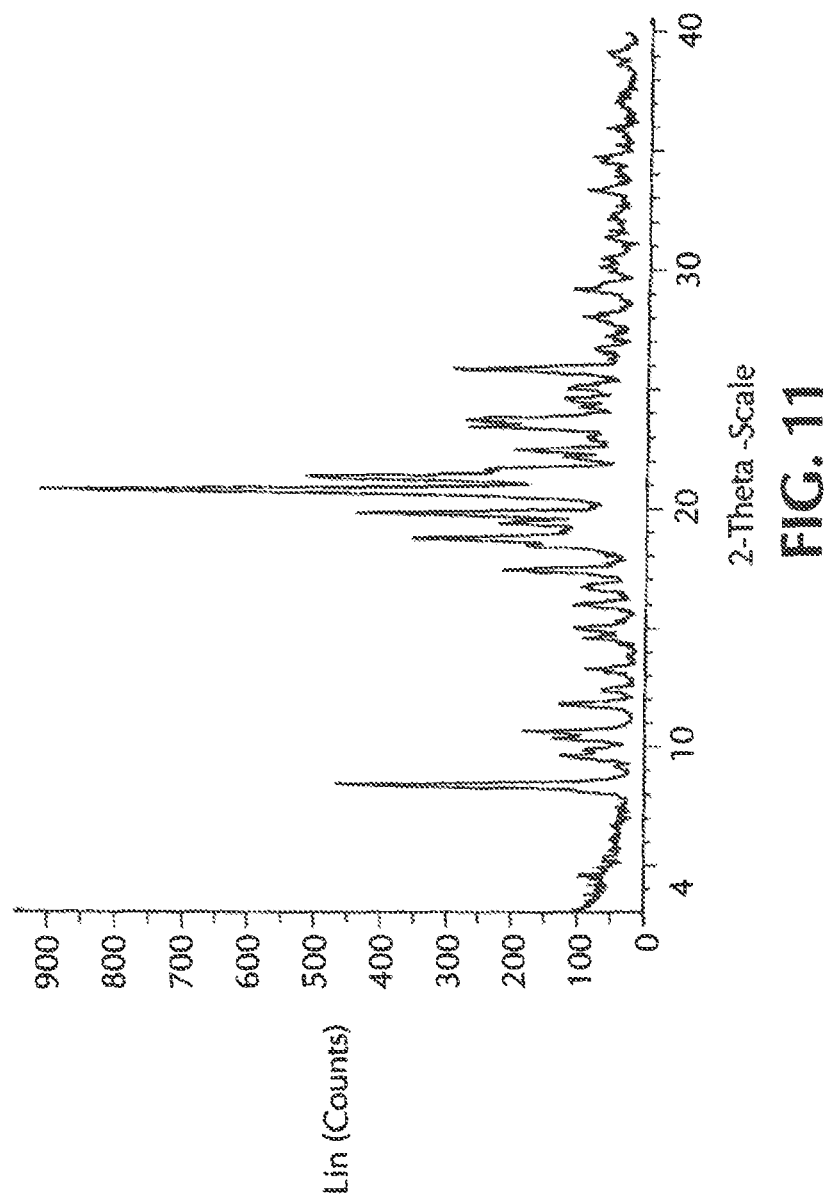
FIG. 11 Diffractogram of atorvastatin dibenzylamine carried out on a Bruker D5000 diffractometer.
Figure 12:
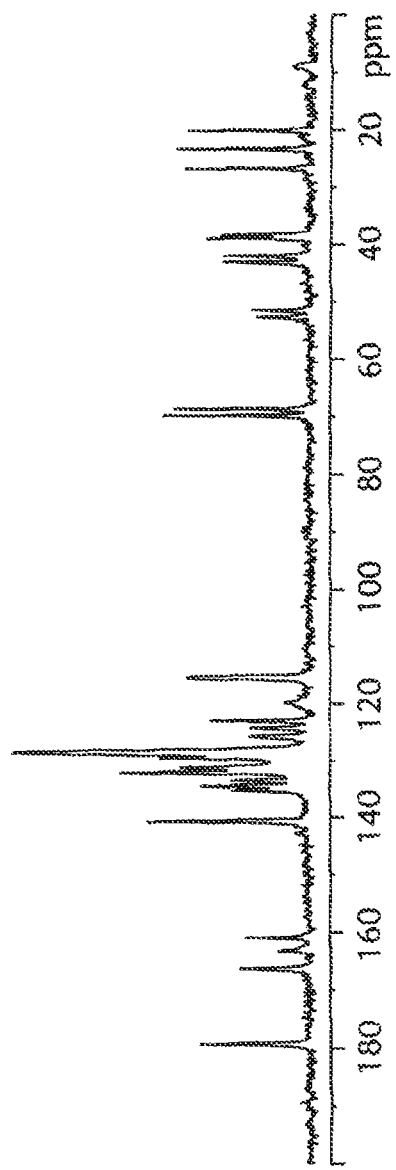
FIG. 12 Solid-state $^{13}$C nuclear magnetic resonance spectrum of atorvastatin dibenzylamine.
Figure 13:
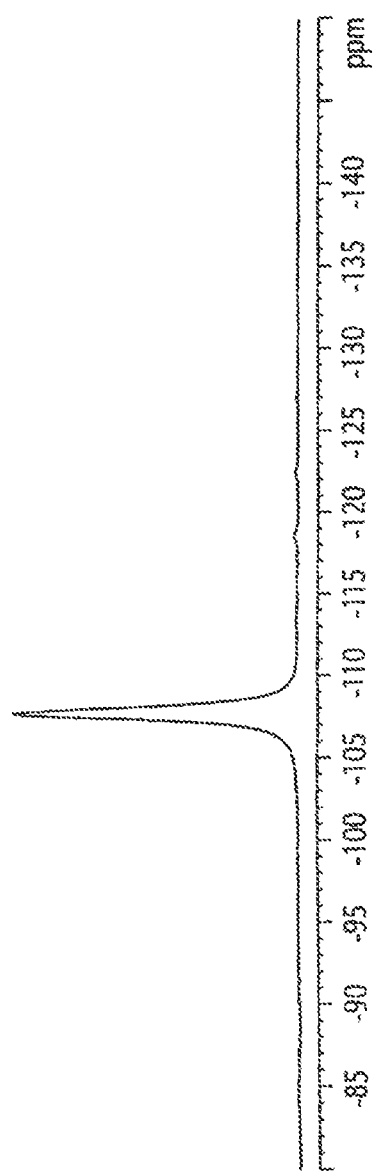
FIG. 13 Solid-state $^{19}$F nuclear magnetic resonance spectrum of atorvastatin dibenzylamine.
Figure 14:
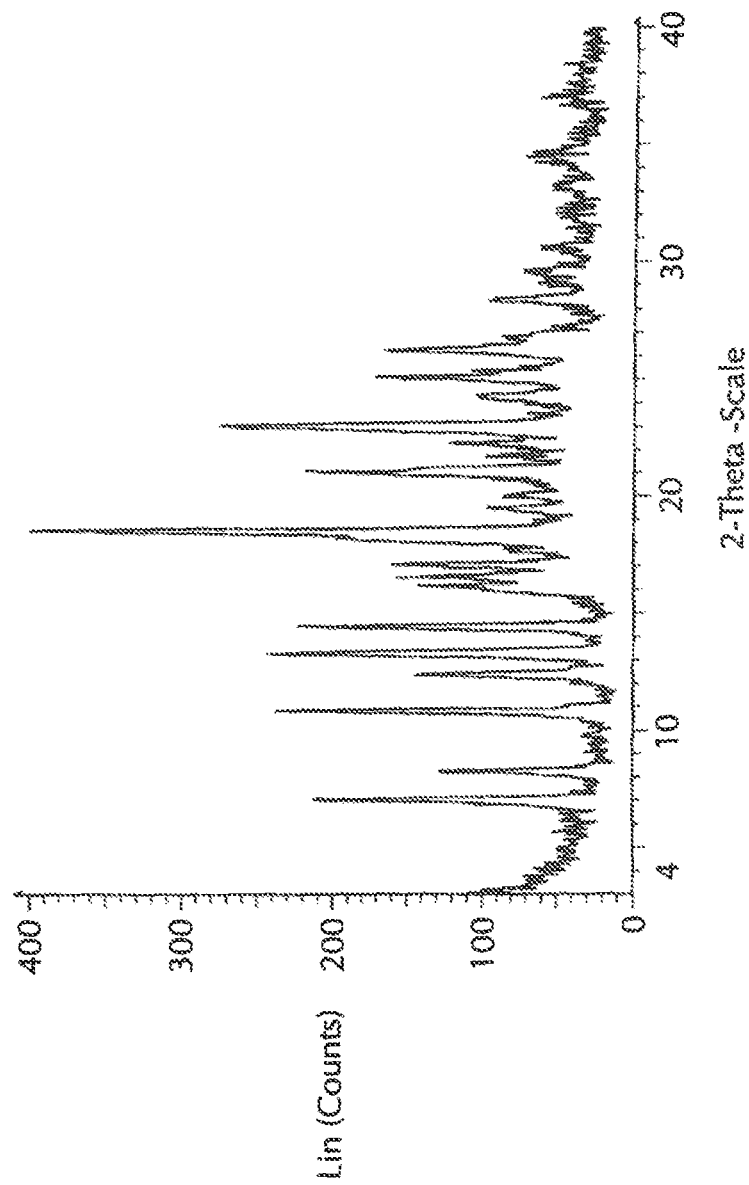
FIG. 14 Diffractogram of Form A atorvastatin diethylamine carried out on a Bruker D5000 diffractometer.
Figure 15:
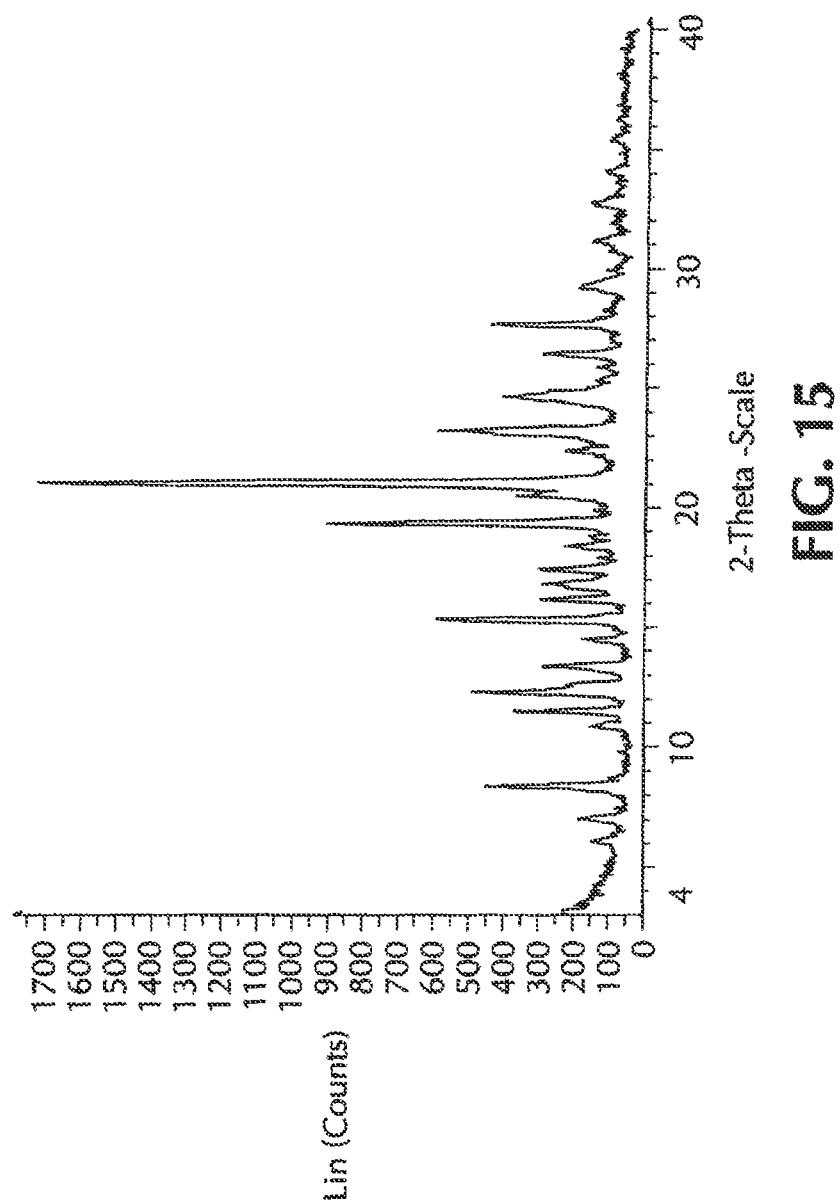
FIG. 15 Diffractogram of Form B atorvastatin diethylamine carried out on a Bruker D5000 diffractometer.
Figure 16:
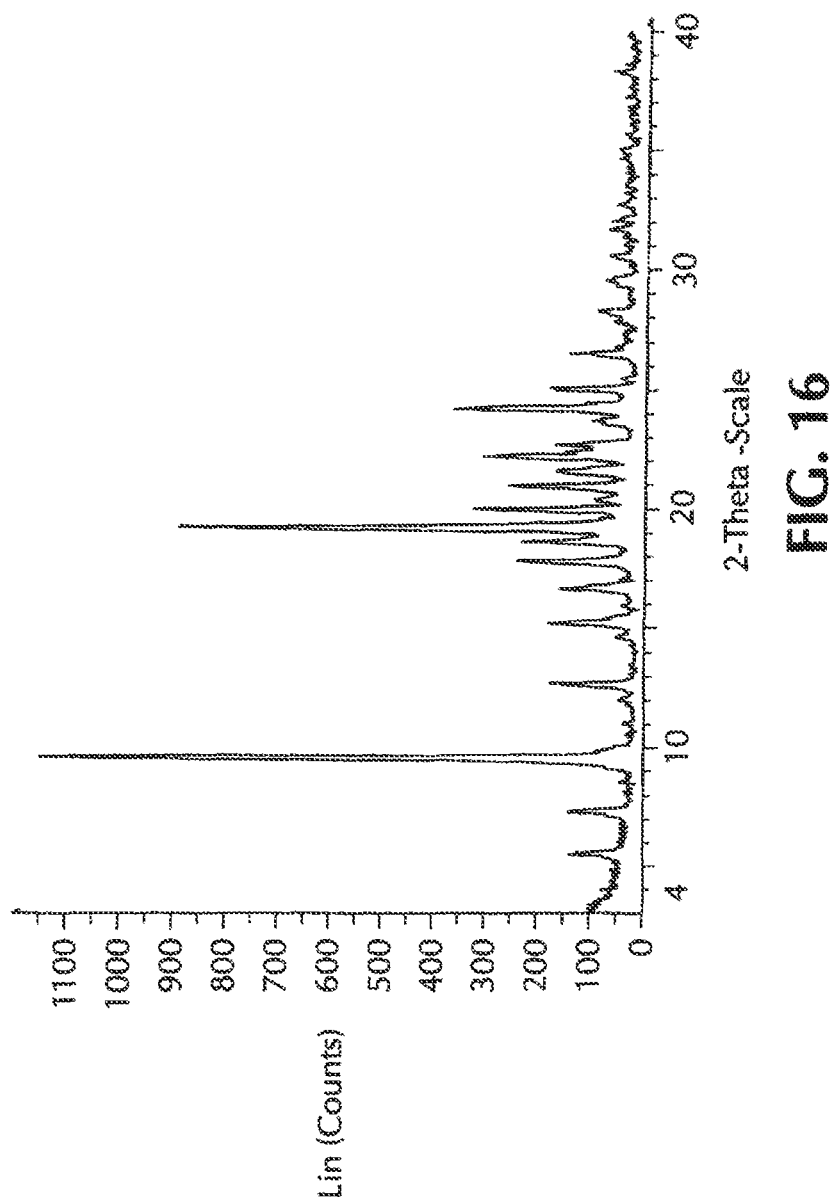
FIG. 16 Diffractogram of atorvastatin erbumine carried out on a Bruker D5000 diffractometer.
Figure 17:
FIG. 17 Solid-state $^{13}$C nuclear magnetic resonance spectrum of atorvastatin erbumine.
Figure 18:
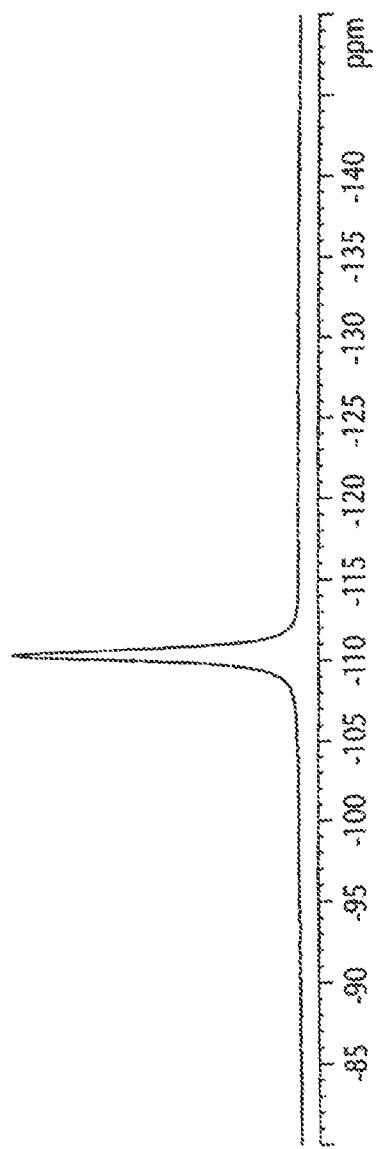
FIG. 18 Solid-state $^{19}$F nuclear magnetic resonance spectrum of atorvastatin erbumine.
Figure 19:
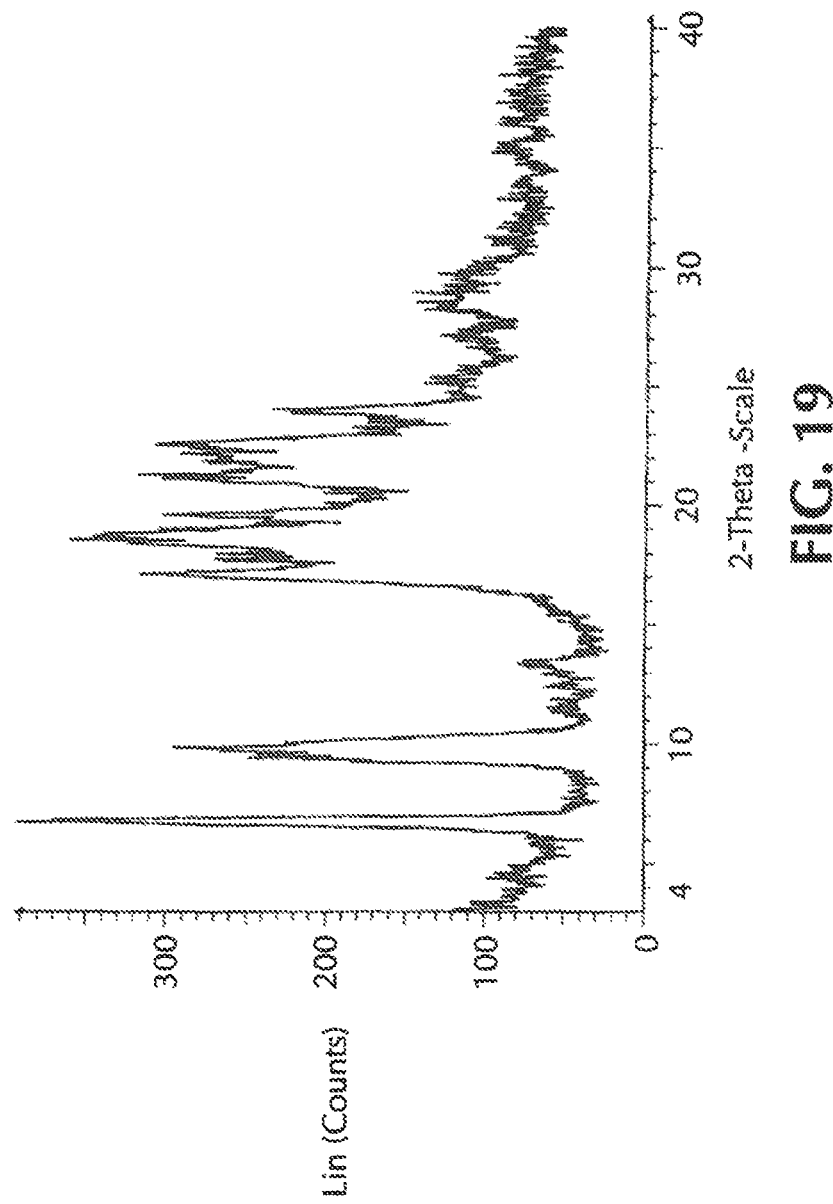
FIG. 19 Diffractogram of atorvastatin L-lysine carried out on a Bruker D5000 diffractometer.
Figure 20:
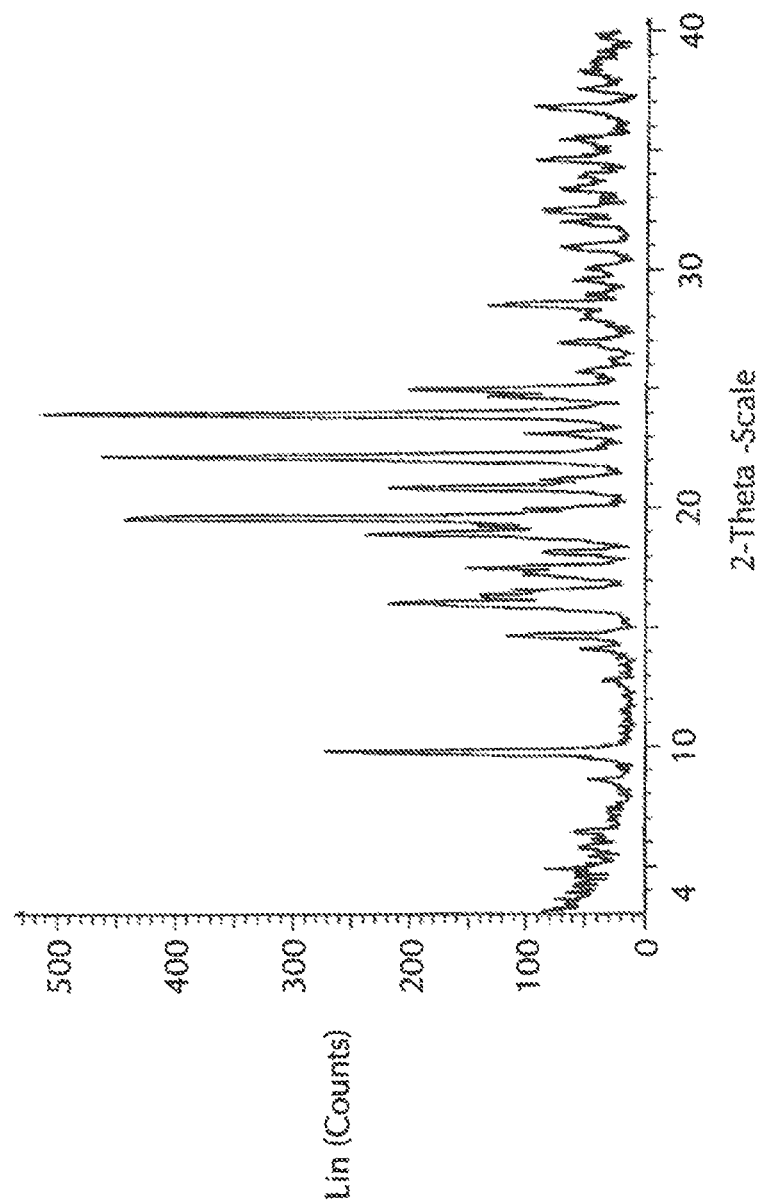
FIG. 20 Diffractogram of atorvastatin morpholine carried out on a Bruker D5000 diffractometer.
Figure 21:
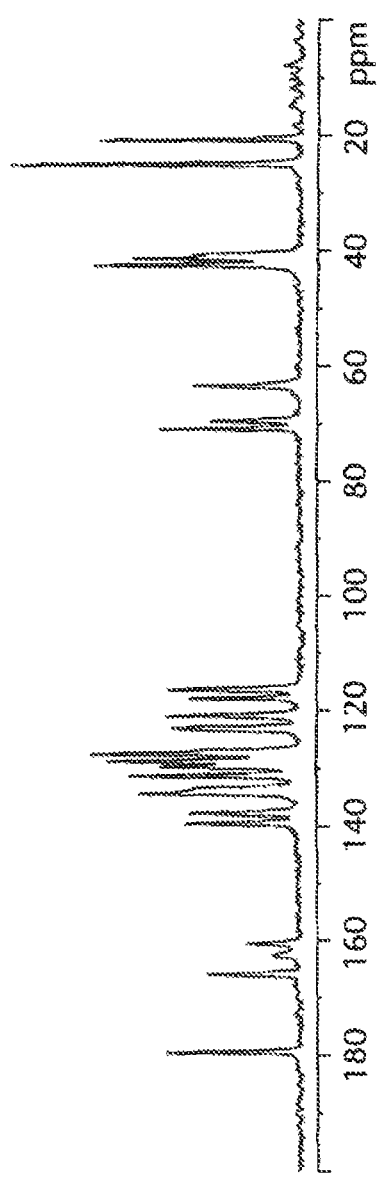
FIG. 21 Solid-state $^{13}$C nuclear magnetic resonance spectrum of atorvastatin morpholine.
Figure 22:
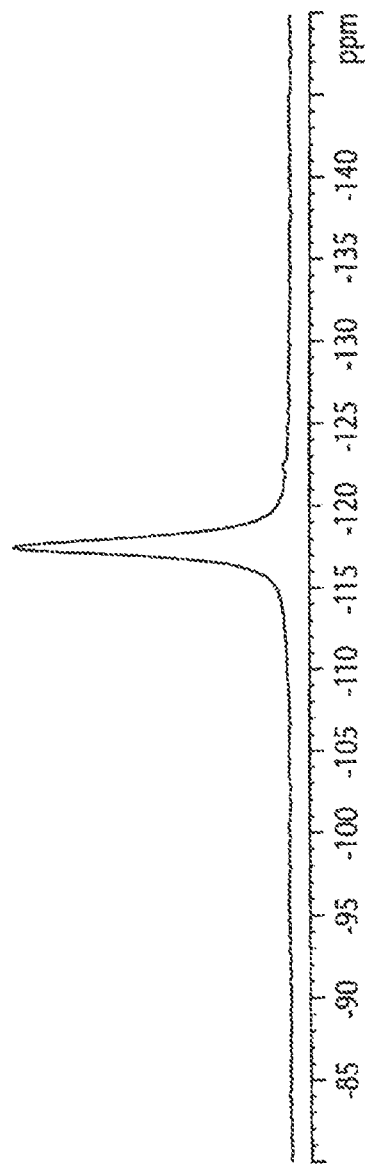
FIG. 22 Solid-state $^{19}$F nuclear magnetic resonance spectrum of atorvastatin morpholine.
Figure 23:
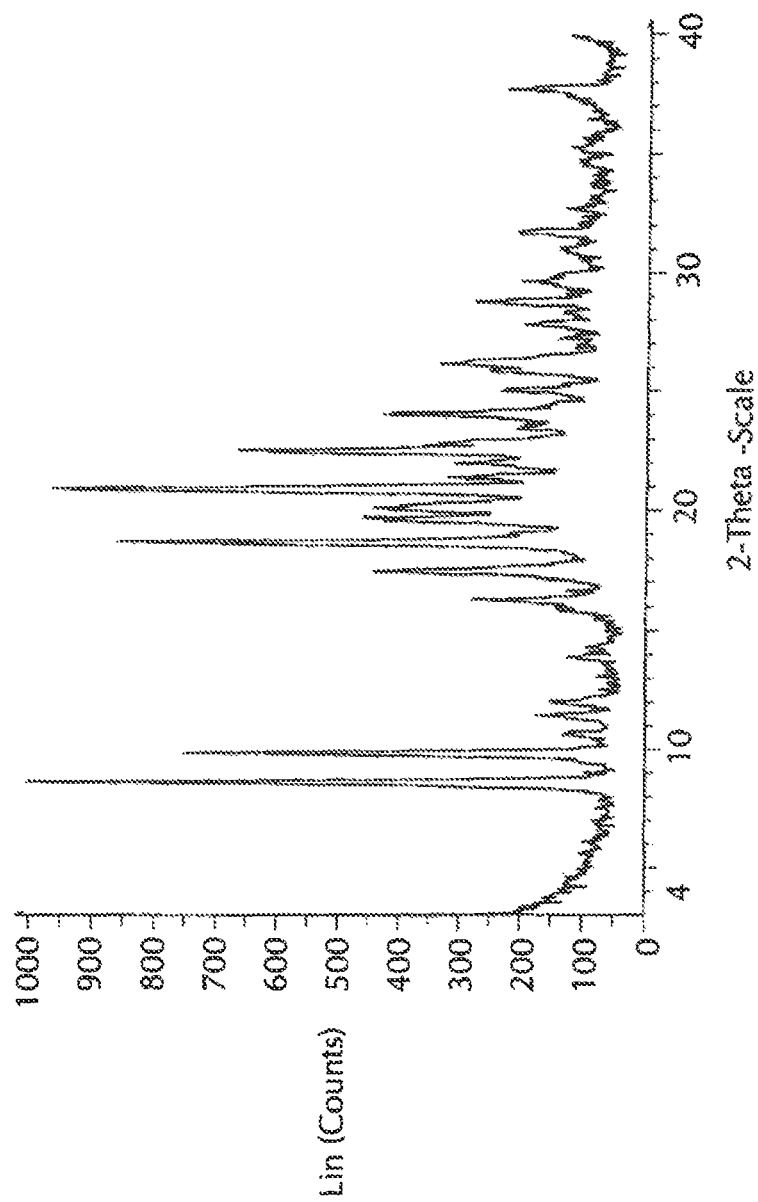
FIG. 23 Diffractogram of atorvastatin olamine carried out on a Bruker D5000 diffractometer.
Figure 24:
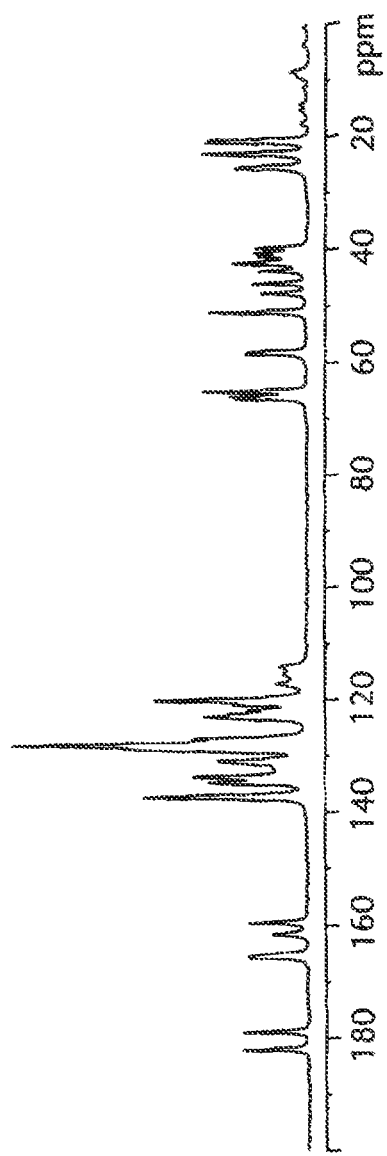
FIG. 24 Solid-state $^{13}$C nuclear magnetic resonance spectrum of atorvastatin olamine.
Figure 25:
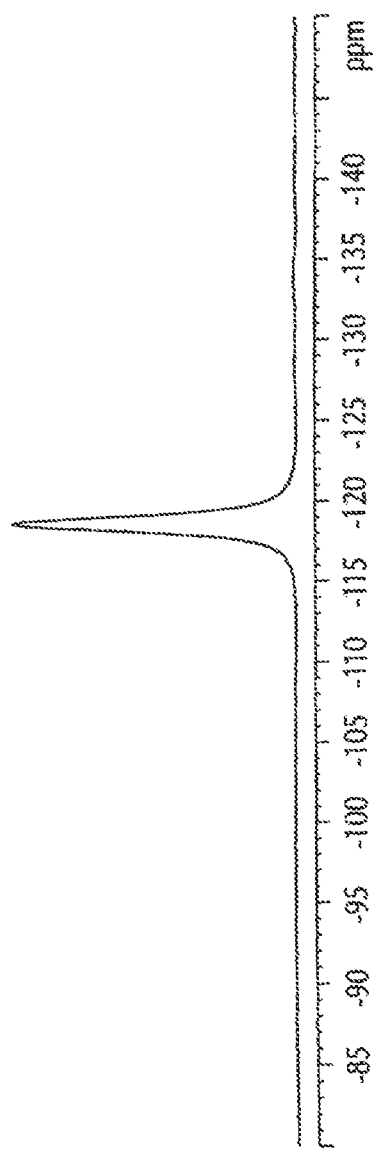
FIG. 25 Solid-state $^{19}$F nuclear magnetic resonance spectrum of atorvastatin olamine.
Figure 26:
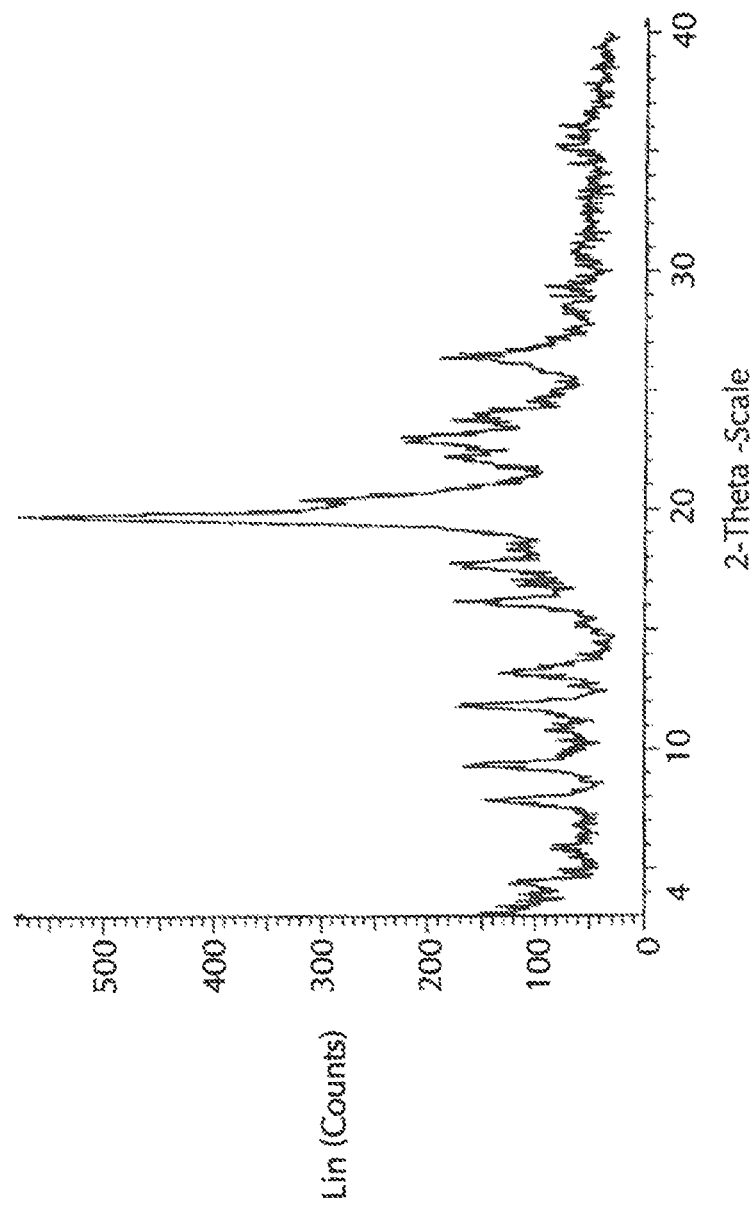
FIG. 26 Diffractogram of atorvastatin piperazine carried out on a Bruker D5000 diffractometer.
Figure 27:
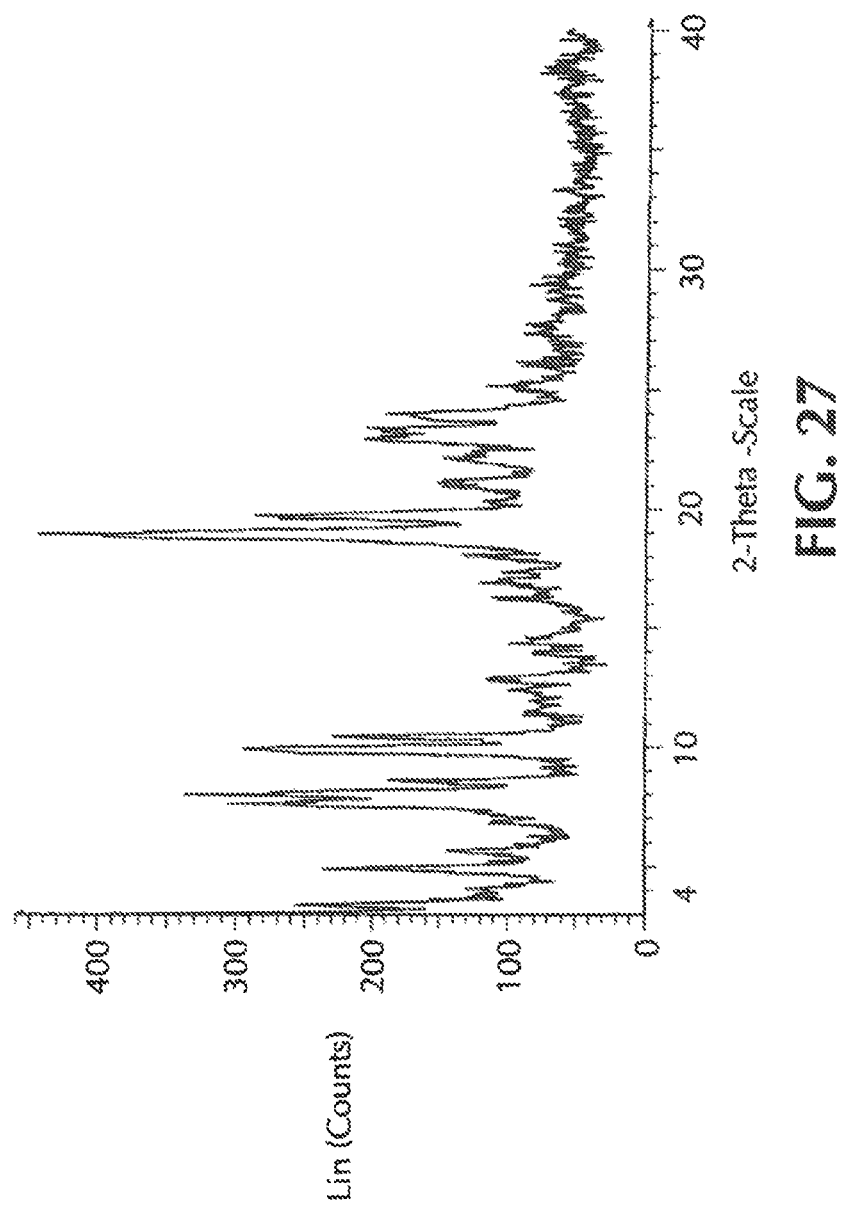
FIG. 27 Diffractogram of atorvastatin sodium carried out on a Bruker D5000 diffractometer.
Figure 28:
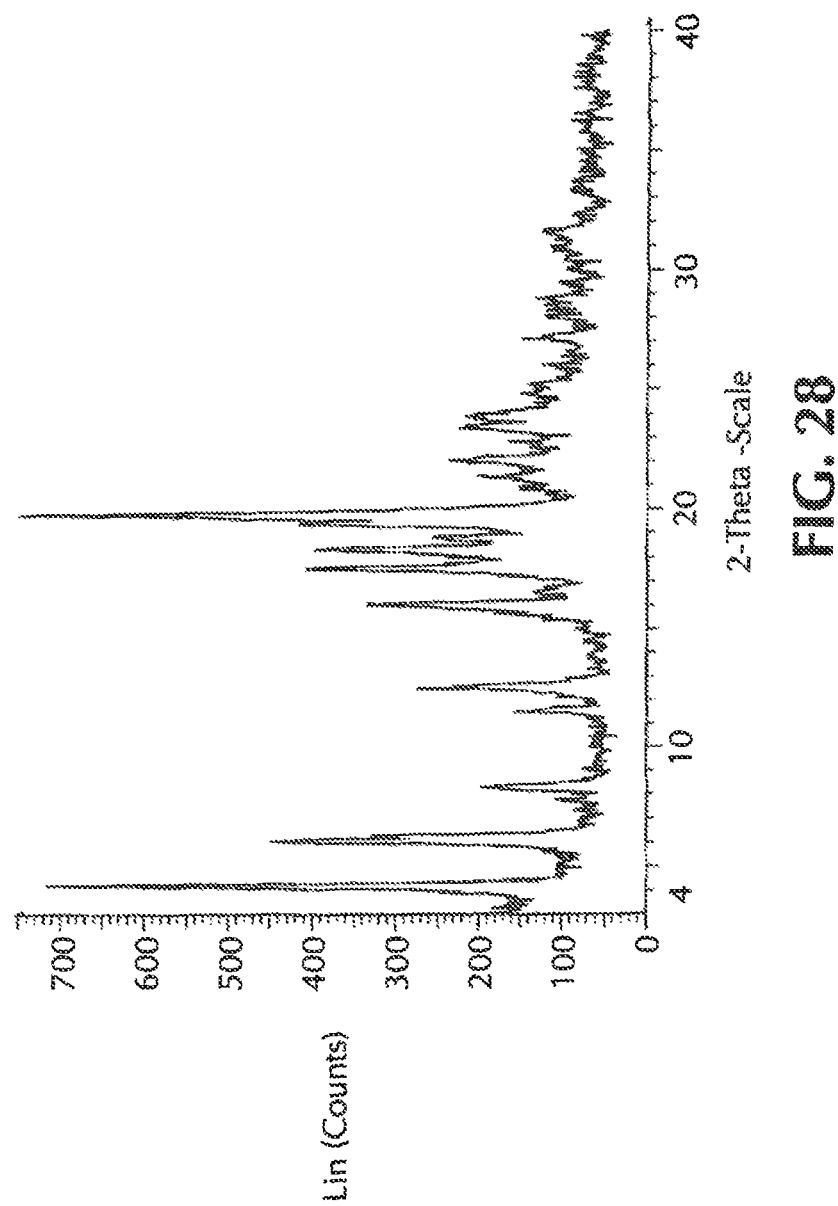
FIG. 28 Diffractogram of atorvastatin 2-amino-2-methylpropan-1-ol carried out on a Bruker D5000 diffractometer.
Figure 29:
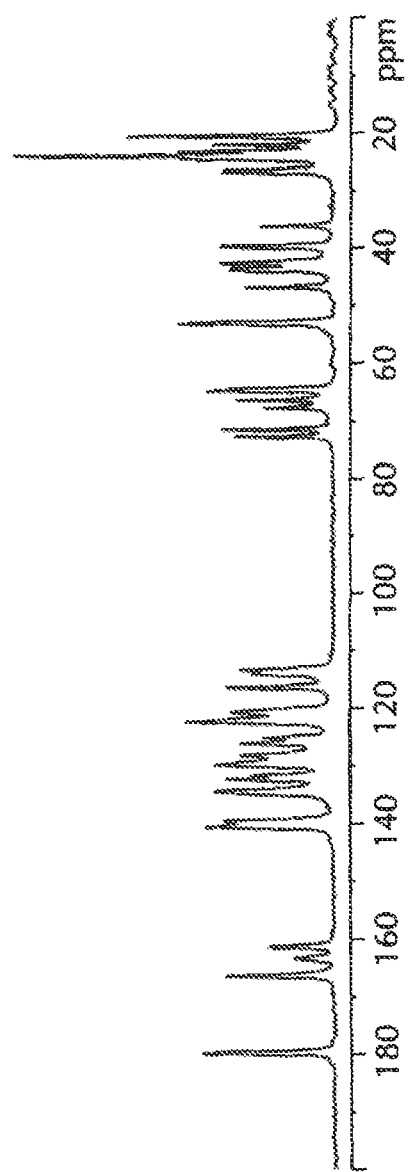
FIG. 29 Solid-state $^{13}$C nuclear magnetic resonance spectrum of atorvastatin 2-amino-2-methylpropan-1-ol.
Figure 30:
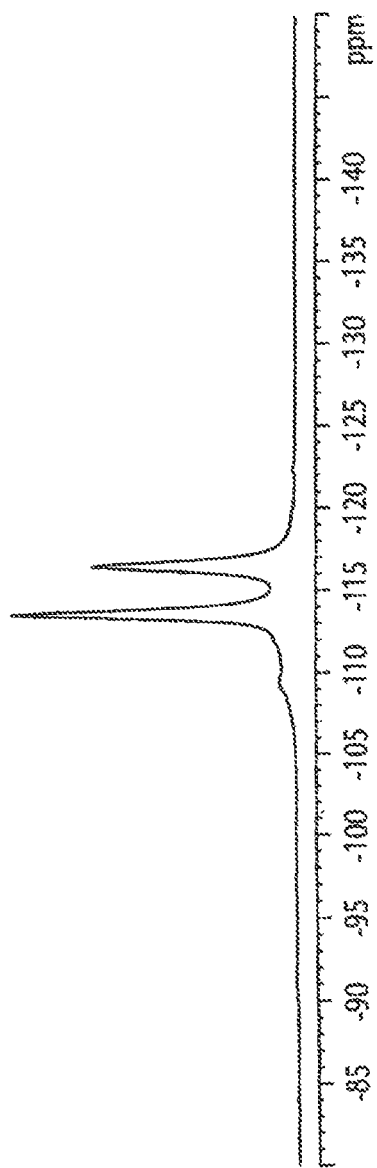
FIG. 30 Solid-state $^{19}$F nuclear magnetic resonance spectrum of atorvastatin 2-amino-2-methylpropan-1-ol.

The novel salt forms of atorvastatin may be characterized by their x-ray powder diffraction patterns and/or by their solid-state nuclear magnetic resonance spectra.

Powder X-Ray Diffraction

Atorvastatin salts were characterized by their powder x-ray diffraction patterns. Thus, the x-ray diffraction pattern was carried out on a Bruker D5000 diffractometer using copper radiation (wavelength 1:1.54056). The tube voltage and amperage were set to 40 kV and 50 mA, respectively. The divergence and scattering slits were set at 1 mm, and the receiving slit was set at 0.6 mm. Diffracted radiation was detected by a Kevex PSI detector. A theta-two theta continuous scan at 2.4°/min (1 sec/0.04° step) from 3.0 to 40° 2θ was used. An alumina standard was analyzed to check the instrument alignment. Data were collected and analyzed using Bruker axis software Version 7.0. Samples were prepared by placing them in a quartz holder. It should be noted that Bruker Instruments purchased Siemans; thus, Bruker D5000 instrument is essentially the same as a Siemans D5000.

The following tables list the 2θ and intensities of lines for the atorvastatin salts and hydrates thereof. Additionally, there are tables which list individual 2θ peaks for the atorvastatin salts and hydrates thereof. In cases were there are two or more crystalline forms of an atorvastatin salt or hydrate thereof, each form can be identified and distinguished from the other crystalline form by either a single x-ray diffraction line, a combination of lines, or a pattern that is different from the x-ray powder diffraction of the other forms.

Table 1 lists the 2θ and relative intensities of all lines that have a relative intensity of >30% in the sample for atorvastatin ammonium and hydrates thereof:

TABLE 1

INTENSITIES AND PEAK LOCATIONS OF
DIFFRACTION LINES IN ATORVASTATIN
AMMONIUM AND HYDRATES THEREOF

| Degree 2θ | Relative Intensity (>30%) |
|---|---|
| 3.5 | 49.0 |
| 4.4 | 34.8 |
| 7.4 | 36.5 |
| 7.8 | 58.0 |
| 8.8 | 53.9 |
| 9.3 | 44.1 |
| 9.9 | 43.8 |
| 10.6 | 80.3 |
| 12.4 | 35.1 |
| 14.1 | 30.1 |
| 16.8 | 54.5 |
| 18.3 | 56.2 |
| 19.0 | 67.8 |
| 19.5 | 100.0 |
| 20.3 | 81.4 |
| 21.4 | 69.0 |
| 21.6 | 63.8 |
| 23.1 | 65.5 |
| 23.9 | 63.8 |
| 24.8 | 69.0 |

Table 2 lists individual peaks for atorvastatin ammonium and hydrates thereof:

TABLE 2

ATORVASTATIN AMMONIUM AND HYDRATES THEREOF
DEGREE
2θ

| |
|---|
| 7.8 |
| 8.8 |
| 9.3 |
| 9.9 |
| 10.6 |
| 12.4 |
| 19.5 |

Table 3 lists the 2θ and relative intensities of all lines that have a relative intensity of >8% in the sample for atorvastatin benethamine Forms A and B and hydrates thereof:

TABLE 3

INTENSITIES AND PEAK LOCATIONS OF DIFFRACTION LINES FOR ATORVASTATIN BENETHAMINE, FORMS A AND B AND HYDRATES THEREOF

| Form A | | Form B | |
|---|---|---|---|
| Degree 2θ | Relative Intensity (>8%) | Degree 2θ | Relative Intensity (>6%) |
| 4.7 | 42.2 | 4.1 | 9.8 |
| 5.3 | 21.7 | 5.0 | 11.3 |
| 6.0 | 12.9 | 5.8 | 8.8 |
| 7.8 | 9.6 | 7.1 | 10.4 |
| 8.9 | 53.3 | 8.4 | 13.3 |
| 9.5 | 84.4 | 8.9 | 53.2 |
| 10.5 | 10.6 | 10.0 | 8.1 |
| 12.0 | 11.5 | 11.6 | 13.6 |
| 13.8 | 12.1 | 12.6 | 16.6 |
| 14.3 | 13.3 | 14.4 | 46.3 |
| 15.6 | 20.1 | 14.8 | 13.5 |
| 16.7 | 24.6 | 16.5 | 15.4 |
| 16.9 | 19.9 | 17.7 | 23.6 |
| 17.6 | 52.7 | 18.6 | 20.2 |
| 17.8 | 53.1 | 20.2 | 100.0 |
| 18.1 | 59.7 | 21.4 | 30.6 |
| 18.8 | 100.0 | 21.6 | 24.7 |
| 19.1 | 39.1 | 22.3 | 5.9 |
| 19.9 | 42.4 | 22.7 | 6.3 |
| 21.3 | 36.2 | 23.4 | 8.4 |
| 21.9 | 22.8 | 23.6 | 12.8 |
| 22.7 | 19.8 | 25.0 | 10.2 |
| 23.6 | 52.4 | 25.2 | 12.2 |
| 24.3 | 23.5 | 25.9 | 19.2 |
| 25.9 | 23.5 | 26.2 | 30.1 |
| 26.3 | 36.2 | 28.0 | 6.9 |
| 27.0 | 13.5 | 28.3 | 5.4 |
| 27.9 | 11.8 | 29.3 | 6.4 |
| 28.8 | 9.4 | 29.7 | 5.9 |
| 29.6 | 9.8 | 31.8 | 5.3 |
| | | 33.5 | 12.1 |
| | | 35.2 | 6.6 |
| | | 35.8 | 5.9 |

Table 4 lists individual 2θ peaks for atorvastatin benethamine, Forms A and B and hydrates thereof.

TABLE 4

FORMS A and B ATORVASTATIN BENETHAMINE AND HYDRATES THEREOF

| Form A Degree 2θ | Form B Degree 2θ |
|---|---|
| 4.7 | 5.0 |
| 5.3 | 7.1 |
| 9.5 | 8.4 |
| 12.0 | 10.0 |
| 15.6 | 11.6 |
| 18.1 | 12.6 |
| 19.9 | 14.8 |
| | 20.2 |

Table 5 lists the 2θ and relative intensities of all lines that have a relative intensity of >9% in the sample for atorvastatin benzathine Forms A, B, and C and hydrates thereof:

TABLE 5

INTENSITIES AND PEAK LOCATIONS OF DIFFRACTION LINES FOR ATORVASTATIN BENZATHINE, FORMS A, B, AND C AND HYDRATES THEREOF

| Form A | | Form B | | Form C | |
|---|---|---|---|---|---|
| Degree 2θ | Relative Intensity (>12%) | Degree 2θ | Relative Intensity (>9%) | Degree 2θ | Relative Intensity (>13%) |
| 9.1 | 97.5 | 8.3 | 100.0 | 3.9 | 59.5 |
| 14.0 | 40.3 | 9.1 | 9.4 | 6.9 | 23.3 |
| 15.1 | 13.8 | 10.2 | 62.6 | 7.9 | 30.5 |
| 15.5 | 13.7 | 11.7 | 9.1 | 9.7 | 70.6 |
| 16.1 | 15.3 | 13.2 | 10.2 | 11.9 | 100.0 |
| 16.4 | 16.8 | 14.4 | 21.1 | 12.8 | 17.8 |
| 18.2 | 40.0 | 15.8 | 18.1 | 13.2 | 41.4 |
| 19.1 | 58.5 | 16.6 | 20.0 | 15.5 | 15.3 |
| 19.6 | 18.1 | 17.1 | 14.8 | 16.3 | 13.1 |
| 20.5 | 100.0 | 18.6 | 34.0 | 16.8 | 17.4 |
| 21.3 | 66.3 | 19.1 | 40.7 | 17.2 | 39.5 |
| 22.1 | 15.5 | 19.4 | 23.0 | 18.9 | 18.4 |
| 22.5 | 21.7 | 19.7 | 14.8 | 19.5 | 31.5 |
| 23.0 | 43.8 | 20.6 | 24.0 | 19.9 | 31.7 |
| 25.2 | 18.8 | 20.9 | 13.1 | 20.4 | 58.2 |
| 25.9 | 12.9 | 21.4 | 28.8 | 20.7 | 43.9 |
| 26.1 | 15.6 | 21.8 | 29.3 | 21.4 | 29.2 |
| 26.5 | 14.4 | 22.3 | 24.9 | 23.0 | 19.0 |
| 28.0 | 14.2 | 22.6 | 29.2 | 23.4 | 18.7 |
| 28.6 | 17.1 | 23.3 | 46.1 | 24.0 | 26.6 |
| | | 23.5 | 31.3 | 24.3 | 33.6 |
| | | 24.3 | 11.0 | 24.6 | 41.4 |
| | | 25.0 | 18.9 | 25.9 | 21.5 |
| | | 26.5 | 14.8 | 26.2 | 28.4 |
| | | 26.8 | 11.6 | | |
| | | 27.4 | 13.2 | | |
| | | 27.9 | 12.3 | | |
| | | 28.2 | 9.3 | | |
| | | 28.9 | 9.3 | | |
| | | 29.1 | 9.8 | | |
| | | 29.7 | 10.9 | | |

Table 6 lists individual 2θ peaks for atorvastatin benzathine, Forms A, B, and C and hydrates thereof.

TABLE 6

FORMS A, B, and C ATORVASTATIN BENZATHINE AND HYDRATES THEREOF

| Form A Degree 2θ | Form B Degree 2θ | Form C Degree 2θ |
|---|---|---|
| 14.0 | 8.3 | 3.9 |
| 15.1 | 10.2 | 6.9 |
| | 14.4 | 7.9 |
| | 15.8 | 9.7 |
| | 18.6 | 12.8 |
| | 21.8 | |
| | 23.3 | |

Table 7 lists the 2θ and relative intensities of all lines that have a relative intensity of >8% in the sample for atorvastatin dibenzylamine and hydrates thereof:

TABLE 7

INTENSITIES AND PEAK LOCATIONS OF DIFFRACTION LINES FOR ATORVASTATIN DIBENZYLAMINE AND HYDRATES THEREOF

| Degree 2θ | Relative Intensity (>8%) |
|---|---|
| 4.6 | 10.6 |
| 8.3 | 50.8 |
| 9.6 | 13.8 |
| 9.8 | 10.0 |
| 10.3 | 14.9 |
| 10.4 | 12.1 |
| 10.6 | 19.8 |
| 11.8 | 13.9 |
| 12.4 | 7.7 |
| 13.3 | 10.0 |
| 14.5 | 10.2 |
| 14.9 | 11.6 |
| 15.9 | 11.8 |
| 16.7 | 10.4 |
| 17.4 | 23.6 |
| 18.4 | 19.7 |
| 18.7 | 38.5 |
| 19.4 | 24.2 |
| 19.8 | 48.0 |
| 20.7 | 100.0 |
| 21.3 | 56.4 |
| 21.6 | 26.7 |
| 22.1 | 13.4 |
| 22.5 | 21.9 |
| 23.0 | 9.7 |
| 23.4 | 29.5 |
| 23.7 | 29.7 |
| 24.3 | 11.0 |
| 24.6 | 13.6 |
| 25.1 | 13.0 |
| 25.8 | 31.9 |
| 26.7 | 8.5 |
| 28.0 | 10.8 |
| 29.2 | 12.2 |
| 33.4 | 9.8 |
| 34.6 | 8.1 |
| 34.8 | 9.1 |

Table 8 lists the individual 2θ peaks for atorvastatin dibenzylamine and hydrates thereof:

TABLE 8

ATORVASTATIN DIBENZYLAMINE AND HYDRATES THEREOF

| Degree 2θ |
|---|
| 8.3 |
| 18.7 |
| 19.8 |
| 20.7 |
| 21.3 |
| 25.8 |

Table 9 lists the 2θ and relative intensities of all lines that have a relative intensity of >8% in the sample for atorvastatin diethylamine Forms A and B and hydrates thereof:

TABLE 9

INTENSITIES AND PEAK LOCATIONS OF DIFFRACTION LINES FOR ATORVASTATIN DIETHYLAMINE, FORMS A AND B AND HYDRATES THEREOF

| Form A | | Form B | |
|---|---|---|---|
| Degree 2θ | Relative Intensity (>20%) | Degree 2θ | Relative Intensity (>8%) |
| 7.0 | 53.0 | 6.1 | 8.3 |
| 8.2 | 32.0 | 7.0 | 10.6 |
| 10.8 | 59.3 | 8.3 | 26.0 |
| 12.3 | 36.0 | 10.8 | 8.5 |
| 13.3 | 60.8 | 11.5 | 21.4 |
| 14.4 | 56.0 | 12.2 | 28.2 |
| 16.1 | 35.5 | 12.5 | 12.7 |
| 16.5 | 39.3 | 13.4 | 16.5 |
| 17.0 | 40.0 | 14.5 | 10.0 |
| 18.2 | 49.3 | 15.3 | 34.2 |
| 18.4 | 100.0 | 16.1 | 17.1 |
| 19.4 | 23.0 | 16.6 | 12.8 |
| 20.0 | 20.5 | 16.8 | 16.6 |
| 21.0 | 54.5 | 17.4 | 17.3 |
| 21.7 | 24.5 | 17.9 | 8.1 |
| 22.3 | 30.5 | 18.4 | 12.8 |
| 23.0 | 68.8 | 18.7 | 8.5 |
| 24.3 | 25.5 | 19.3 | 52.2 |
| 25.1 | 38.5 | 20.5 | 21.4 |
| 25.4 | 26.9 | 21.0 | 100.0 |
| 26.3 | 41.3 | 22.3 | 13.0 |
| 26.8 | 21.8 | 23.2 | 34.2 |
| 28.4 | 23.8 | 24.6 | 23.7 |
| | | 25.4 | 8.2 |
| | | 25.9 | 8.1 |
| | | 26.4 | 16.9 |
| | | 27.6 | 25.6 |
| | | 29.2 | 10.6 |
| | | 31.2 | 8.5 |
| | | 32.8 | 9.1 |

Table 10 lists individual 2θ peaks for atorvastatin diethylamine, Forms A, B, and C and hydrates thereof.

TABLE 10

FORMS A AND B ATORVASTATIN DIETHYLAMINE AND HYDRATES THEREOF

| Form A Degree 2θ | Form B Degree 2θ |
|---|---|
| 17.0 | 6.1 |
| 18.2 | 11.5 |
| 20.0 | 15.3 |
| 21.7 | 17.4 |
| 23.0 | 20.5 |
| | 23.2 |
| | 27.6 |

Table 11 lists the 2θ and relative intensities of all lines that have a relative intensity >6% in the sample for atorvastatin erbumine and hydrates thereof:

TABLE 11

INTENSITIES AND PEAK LOCATIONS OF DIFFRACTION LINES FOR ATORVASTATIN ERBUMINE AND HYDRATES THEREOF

| Degree 2θ | Relative Intensity (>6%) |
|---|---|
| 5.4 | 11.9 |
| 7.3 | 12.0 |
| 9.5 | 100.0 |
| 12.6 | 14.3 |
| 15.2 | 15.6 |
| 16.6 | 13.7 |
| 17.8 | 21.0 |
| 18.6 | 20.2 |
| 19.2 | 77.6 |
| 20.0 | 28.3 |
| 20.4 | 8.2 |
| 20.9 | 22.3 |
| 21.6 | 14.3 |
| 22.2 | 26.6 |
| 22.4 | 13.3 |
| 22.6 | 14.5 |
| 23.7 | 8.7 |
| 24.2 | 31.6 |
| 25.0 | 15.5 |
| 26.5 | 12.3 |
| 28.2 | 7.9 |
| 29.5 | 6.3 |
| 30.6 | 6.5 |

Table 12 lists individual 2θ peaks for atorvastatin erbumine and hydrates thereof:

TABLE 12

ATORVASTATIN ERBUMINE AND HYDRATES THEREOF

| Degree 2θ |
|---|
| 5.4 |
| 7.3 |
| 9.5 |
| 17.8 |
| 19.2 |
| 20.0 |
| 22.2 |
| 24.2 |

Table 13 lists 2θ and relative intensities of all lines that have a relative intensity of >40% in the sample for atorvastatin L-lysine and hydrates thereof:

TABLE 13

INTENSITIES AND PEAK LOCATIONS OF DIFFRACTION LINES FOR ATORVASTATIN L-LYSINE AND HYDRATES THEREOF

| Degree 2θ | Relative Intensity (>40%) |
|---|---|
| 6.7 | 100.0 |
| 9.5 | 62.1 |
| 9.8 | 74.3 |
| 17.1 | 80.4 |
| 18.7 | 86.5 |
| 19.6 | 76.8 |
| 21.1 | 77.1 |
| 22.1 | 72.1 |
| 22.5 | 77.9 |
| 24.0 | 59.5 |

Table 14 lists individual 2θ peaks for atorvastatin L-Lysine and hydrates thereof:

TABLE 14

ATORVASTATIN L-LYSINE AND HYDRATES THEREOF

| Degree 2θ |
|---|
| 6.7 |
| 9.8 |
| 17.1 |
| 24.0 |

Table 15 lists the 2θ and relative intensities of all lines that have a relative intensity of >9% in the sample for atorvastatin morpholine and hydrates thereof:

TABLE 15

INTENSITIES AND PEAK LOCATIONS OF DIFFRACTION LINES FOR ATORVASTATIN MORPHOLINE AND HYDRATES THEREOF

| Degree 2θ | Relative Intensity (>9%) |
|---|---|
| 4.8 | 15.9 |
| 5.7 | 10.7 |
| 6.4 | 11.6 |
| 8.6 | 9.2 |
| 9.7 | 52.5 |
| 12.8 | 6.8 |
| 14.1 | 10.3 |
| 14.6 | 22.5 |
| 16.0 | 42.1 |
| 16.3 | 26.7 |
| 16.5 | 21.3 |
| 17.3 | 19.6 |
| 17.5 | 29.3 |
| 18.1 | 16.5 |
| 18.9 | 46.1 |
| 19.2 | 27.3 |
| 19.6 | 85.9 |
| 19.9 | 19.8 |
| 20.8 | 42.2 |
| 21.2 | 16.9 |
| 22.1 | 89.9 |
| 23.1 | 19.6 |
| 23.9 | 100.0 |
| 24.6 | 26.0 |
| 25.0 | 39.0 |
| 25.7 | 11.0 |
| 27.0 | 14.1 |
| 28.1 | 10.1 |
| 28.5 | 25.8 |
| 29.6 | 11.8 |
| 30.1 | 9.9 |
| 30.9 | 13.4 |
| 31.0 | 14.1 |
| 32.0 | 13.0 |
| 32.4 | 16.5 |
| 33.4 | 14.1 |
| 33.9 | 11.0 |
| 34.6 | 18.0 |
| 35.4 | 14.3 |
| 36.8 | 18.2 |
| 37.6 | 11.4 |

Table 16 lists individual 2θ peaks for atorvastatin morpholine and hydrates thereof:

TABLE 16

ATORVASTATIN MORPHOLINE AND HYDRATES THEREOF
Degree
2θ

| Degree 2θ |
|---|
| 9.7 |
| 16.0 |
| 18.9 |
| 19.6 |
| 20.8 |
| 22.1 |
| 23.9 |
| 25.0 |

Table 17 lists the 2θ and relative intensities of all lines that have a relative intensity of >15% in the sample for atoraystatin olamine and hydrates thereof:

TABLE 17

INTENSITIES AND PEAK LOCATIONS OF DIFFRACTION LINES FOR ATORVASTATIN OLAMINE AND HYDRATES THEREOF

| Degree 2θ | Relative Intensity (>15%) |
|---|---|
| 8.5 | 100.0 |
| 9.8 | 74.7 |
| 11.4 | 17.3 |
| 12.0 | 15.6 |
| 16.3 | 27.7 |
| 17.4 | 43.9 |
| 18.6 | 85.5 |
| 19.6 | 45.8 |
| 20.1 | 43.9 |
| 20.9 | 96.0 |
| 21.4 | 31.6 |
| 22.0 | 30.5 |
| 22.5 | 66.1 |
| 22.8 | 35.6 |
| 23.5 | 20.5 |
| 24.1 | 42.7 |
| 25.1 | 23.3 |
| 25.9 | 25.0 |
| 26.2 | 33.1 |
| 27.8 | 19.3 |
| 28.8 | 27.5 |
| 29.6 | 20.0 |
| 31.7 | 20.5 |
| 37.7 | 22.5 |

Table 18 lists individual 2θ peaks for atorvastatin olamine and hydrates thereof:

TABLE 18

ATORVASTATIN OLAMINE AND HYDRATES THEREOF
Degree
2θ

| Degree 2θ |
|---|
| 8.5 |
| 9.8 |
| 17.4 |
| 18.6 |
| 20.9 |
| 22.5 |
| 24.1 |

Table 19 lists the 2θ and relative intensities of all lines that have a relative intensity of >20% in the sample for atorvastatin piperazine and hydrates thereof:

TABLE 19

INTENSITIES AND PEAK LOCATIONS OF DIFFRACTION LINES FOR ATORVASTATIN PIPERAZINE AND HYDRATES THEREOF

| Degree 2θ | Relative Intensity (>20%) |
|---|---|
| 4.4 | 20.4 |
| 7.8 | 25.5 |
| 9.3 | 27.2 |
| 11.8 | 29.7 |
| 13.2 | 22.9 |
| 16.1 | 30.0 |
| 17.7 | 30.9 |
| 19.7 | 100.0 |
| 20.4 | 55.0 |
| 22.2 | 31.9 |
| 22.9 | 36.2 |
| 23.8 | 30.7 |
| 26.4 | 32.6 |

Table 20 lists the individual 2θ peaks for atorvastatin piperazine and hydrates thereof:

TABLE 20

ATORVASTATIN PIPERAZINE AND HYDRATES THEREOF
Degree
2θ

| Degree 2θ |
|---|
| 7.8 |
| 9.3 |
| 11.8 |
| 16.1 |
| 19.7 |

Table 21 lists the 2θ and relative intensities of all lines that have a relative intensity of >25% in the sample for atoravastatin sodium and hydrates thereof:

TABLE 21

INTENSITIES AND PEAK LOCATIONS OF DIFFRACTION LINES FOR ATORVASTATIN SODIUM AND HYDRATES THEREOF

| Degree 2θ | Relative Intensity (>25%) |
|---|---|
| 3.4 | 57.8 |
| 4.1 | 29.2 |
| 4.9 | 53.0 |
| 5.6 | 32.4 |
| 6.8 | 25.2 |
| 7.6 | 68.5 |
| 8.0 | 75.7 |
| 8.5 | 42.0 |
| 9.9 | 66.1 |
| 10.4 | 51.5 |
| 12.8 | 25.5 |
| 18.9 | 100.0 |
| 19.7 | 64.5 |
| 21.2 | 32.8 |
| 22.1 | 33.3 |
| 22.9 | 45.4 |
| 23.3 | 43.6 |
| 24.0 | 42.7 |
| 25.2 | 26.1 |

Table 22 lists individual 2θ peaks for atorvastatin sodium and hydrates thereof:

TABLE 22

ATORVASTATIN SODIUM AND HYDRATES THEREOF
Degree 2θ

| |
|---|
| 3.4 |
| 4.9 |
| 7.6 |
| 8.0 |
| 9.9 |
| 18.9 |
| 19.7 |

Table 23 lists the 2θ and relative intensities of all lines that have a relative intensity of >25% in the sample for atorvastatin 2-amino-2-methylpropan-1-ol and hydrates thereof:

TABLE 23

INTENSITIES AND PEAK LOCATIONS OF DIFFRACTION LINES FOR ATORVASTATIN 2-AMINO-2-METHYLPROPAN-1-OL AND HYDRATES THEREOF

| Degree 2θ | Relative Intensity (>20%) |
|---|---|
| 4.2 | 95.2 |
| 6.0 | 59.9 |
| 6.2 | 43.7 |
| 8.3 | 26.3 |
| 11.5 | 20.9 |
| 12.5 | 36.5 |
| 12.6 | 31.1 |
| 16.0 | 44.4 |
| 17.5 | 54.3 |
| 18.3 | 52.8 |
| 18.8 | 34.0 |
| 19.4 | 55.3 |
| 19.7 | 100.0 |
| 21.3 | 26.7 |
| 22.0 | 31.3 |
| 22.8 | 21.7 |
| 23.4 | 29.7 |
| 23.8 | 28.6 |

Table 24 lists individual peaks for atorvastatin 2-amino-2-methylpropan-1-ol and hydrates thereof:

TABLE 24

ATORVASTATIN 2-AMINO-2-METHYLPROPAN-1-OL AND HYDRATES THEREOF
Degree 2θ

| |
|---|
| 4.2 |
| 8.3 |
| 16.0 |
| 17.5 |
| 18.3 |
| 19.4 |
| 19.7 |

Solid State Nuclear Magnetic Resonance

The novel salt forms of atorvastatin may also be characterized by their solid-state nuclear magnetic resonance spectra. Thus, the solid-state nuclear magnetic resonance spectra of the salt forms of atorvastatin were carried out on a Bruker-Biospin Avance DSX 500 MHz NMR spectrometer.

$^{19}$F SSNMR

Approximately 15 mg of sample were tightly packed into a 2.5 mm ZrO spinner for each sample analyzed. One-dimensional $^{19}$F spectra were collected at 295 K and ambient pressure on a Bruker-Biospin 2.5 mm BL cross-polarization magic angle spinning (CPMAS) probe positioned into a wide-bore Bruker-Biospin Avance DSX 500 MHz NMR spectrometer. The samples were positioned at the magic angle and spun at 35.0 kHz with no cross-polarization from protons, corresponding to the maximum specified spinning speed for the 2.5 mm spinners. The fast spinning speed minimized the intensities of the spinning side bands and provided almost complete decoupling of $^{19}$F signals from protons. The number of scans were individually adjusted for each sample to obtain adequate single/noise (S/N). Typically, 150 scans were acquired. Prior to $^{19}$F acquisition, $^{19}$F relaxation times were measured by an inversion recovery technique. The recycle delay for each sample was then adjusted to five times the longest $^{19}$F relaxation time in the sample, which ensured acquisition of quantitative spectra. A fluorine probe background was subtracted in each alternate scan after presaturating the $^{19}$F signal. The spectra were referenced using an external sample of trifluoroacetic acid (diluted to 50% V/V by $H_2O$), setting its resonance to –76.54 ppm.

$^{13}$C SSNMR

Approximately 80 mg of sample were tightly packed into a 4 mm ZrO spinner for each sample analyzed. One-dimensional $^{13}$C spectra were collected at ambient pressure using $^1$H-$^{13}$C CPMAS at 295 K on a Bruker 4 mm BL CPMAS probe positioned into a wide-bore Bruker-Biospin Avance DSX 500 MHZ NMR spectrometer. The samples were spun at 15.0 kHz corresponding to the maximum specified spinning speed for the 7 mm spinners. The fast spinning speed minimized the intensities of the spinning side bands. To optimize the signal sensitivity, the cross-polarization contact time was adjusted to 1.5 ms, and the proton decoupling power was set to 100 kHz. The number of scans were individually adjusted for each sample to obtain adequate S/N. Typically, 1900 scans were acquired with a recycle delay of 5 seconds. The spectra were referenced using an external sample of adamantane, setting its upfield resonance at 29.5 ppm.

Table 25 and Table 25a lists the $^{13}$C NMR chemical shifts for Form A and B atorvastatin benethamine and hydrates thereof:

TABLE 25

FORM A BENETHAMINE AND HYDRATES THEREOF

| Peak # | ppm* |
|---|---|
| 1 | 180.1 |
| 2 | 178.8 |
| 3 | 165.1 |
| 4 | 164.1 |
| 5 | 162.8 |
| 6 | 161.7 |
| 7 | 160.7 |
| 8 | 140.6 |
| 9 | 139.6 |
| 10 | 137.9 |
| 11 | 136.1 |
| 12 | 133.0 |
| 13 | 129.6 |
| 14 | 127.3 |
| 15 | 126.4 |
| 16 | 125.4 |
| 17 | 123.1 |
| 18 | 122.5 |
| 19 | 121.6 |
| 20 | 121.1 |
| 21 | 119.9 |
| 22 | 116.4 |
| 23 | 115.4 |

TABLE 25-continued

FORM A BENETHAMINE AND HYDRATES THEREOF

| Peak # | ppm* |
|---|---|
| 24 | 114.5 |
| 25 | 114.0 |
| 26 | 66.0 |
| 27 | 65.5 |
| 28 | 64.6 |
| 29 | 53.6 |
| 30 | 51.5 |
| 31 | 51.0 |
| 32 | 47.8 |
| 33 | 44.6 |
| 34 | 43.3 |
| 35 | 41.4 |
| 36 | 40.9 |
| 37 | 38.5 |
| 38 | 37.7 |
| 39 | 36.8 |
| 40 | 34.0 |
| 41 | 32.7 |
| 42 | 26.5 |
| 43 | 25.1 |
| 44 | 23.5 |
| 45 | 23.1 |
| 46 | 19.7 |
| 47 | 19.1 |

*Values in ppm with respect to trimethylsilane (TMS) at 0 ppm; referenced using an external sample of adamantane, setting is upfield resonance to 29.5 ppm.

TABLE 25a

FORM B BENETHAMINE AND HYDRATES THEREOF

| Peak # | ppm* |
|---|---|
| 1 | 179.4 |
| 2 | 165.6 |
| 3 | 162.4 |
| 4 | 140.1 |
| 5 | 138.6 |
| 6 | 133.6 |
| 7 | 132.8 |
| 8 | 129.9 |
| 9 | 128.2 |
| 10 | 125.7 |
| 11 | 123.6 |
| 12 | 114.8 |
| 13 | 69.6 |
| 14 | 69.0 |
| 15 | 52.3 |
| 16 | 49.8 |
| 17 | 43.1 |
| 18 | 42.2 |
| 19 | 39.6 |
| 20 | 38.9 |
| 21 | 31.5 |
| 22 | 26.5 |
| 23 | 23.5 |
| 24 | 19.6 |

*Values in ppm with respect to trimethylsilane (TMS) at 0 ppm; referenced using an external sample of adamantane, setting is upfield resonance to 29.5 ppm.

Table 26 lists individual $^{13}$C NMR chemical shifts for Form A atorvastatin benethamine:

TABLE 26

FORM A ATORVASTATIN BENETHAMINE AND HYDRATES THEREOF

| Peak # | ppm* |
|---|---|
| 1 | 180.1 |
| 2 | 178.8 |
| 3 | 165.1 |
| 4 | 164.1 |
| 5 | 161.7 |
| 6 | 160.7 |
| 7 | 26.5 |
| 8 | 25.1 |
| 9 | 23.5 |
| 10 | 23.1 |
| 11 | 19.7 |
| 12 | 19.1 |

*Values in ppm with respect to trimethylsilane (TMS) at 0 ppm; referenced using an external sample of adamantane, setting is upfield resonance to 29.5 ppm.

Table 27 lists individual $^{13}$C NMR chemical shifts for Form B atorvastatin benethamine:

TABLE 27

FORM B ATORVASTATIN BENETHAMINE AND HYDRATES THEREOF

| Peak # | ppm* |
|---|---|
| 1 | 179.4 |
| 2 | 165.6 |
| 22 | 26.5 |
| 23 | 23.5 |
| 24 | 19.6 |

*Values in ppm with respect to trimethylsilane (TMS) at 0 ppm; referenced using an external sample of adamantane, setting is upfield resonance to 29.5 ppm.

Table 28 and 28a lists the $^{19}$F NMR chemical shifts for Forms A and B atorvastatin benethamine and hydrates thereof:

TABLE 28

FORM A ATORVASTATIN BENETHAMINE AND HYDRATES THEREOF

| Peak # | ppm* |
|---|---|
| 1 | −113.2 |
| 2 | −114.2 |

*Values in ppm with respect to CCl$_3$F at 0 ppm, referenced using an external standard of trifluoroacetic acid (50% V/V in water) at −76.54 ppm.

TABLE 28a

FORM B ATORVASTATIN BENETHAMINE AND HYDRATES THEREOF

| Peak # | ppm* |
|---|---|
| 1 | −113.7 |
| 2 | −114.4 |

*Values in ppm with respect to CCl$_3$F at 0 ppm, referenced using an external standard of trifluoroacetic acid (50% V/V in water) at −76.54 ppm.

Table 29 lists the $^{13}$C NMR chemical shifts for atorvastatin dibenzylamine and hydrates thereof:

TABLE 29

ATORVASTATIN DIBENZYLAMINE AND HYDRATES THEREOF

| Peak # | ppm* |
|---|---|
| 1 | 179.1 |
| 2 | 166.2 |

TABLE 29-continued

ATORVASTATIN DIBENZYLAMINE AND HYDRATES THEREOF

| Peak # | ppm* |
|---|---|
| 3 | 163.1 |
| 4 | 160.8 |
| 5 | 140.6 |
| 6 | 135.2 |
| 7 | 134.3 |
| 8 | 133.4 |
| 9 | 131.9 |
| 10 | 131.1 |
| 11 | 129.4 |
| 12 | 128.3 |
| 13 | 125.6 |
| 14 | 124.2 |
| 15 | 122.9 |
| 16 | 119.7 |
| 17 | 115.4 |
| 18 | 69.7 |
| 19 | 68.6 |
| 20 | 52.6 |
| 21 | 51.3 |
| 22 | 43.0 |
| 23 | 41.9 |
| 24 | 38.8 |
| 25 | 38.2 |
| 26 | 26.7 |
| 27 | 23.3 |
| 28 | 20.0 |

*Values in ppm with respect to trimethylsilane (TMS) at 0 ppm; referenced using an external sample of adamantane, setting is upfield resonance to 29.5 ppm.

Table 30 lists individual $^{13}$C NMR chemical shifts for atorvastatin dibenzylamine and hydrates thereof:

TABLE 30

ATORVASTATIN DIBENZYLAMINE AND HYDRATES THEREOF

| Peak # | ppm* |
|---|---|
| 1 | 179.1 |
| 2 | 166.2 |
| 3 | 163.1 |
| 4 | 160.8 |
| 26 | 26.7 |
| 27 | 23.3 |
| 28 | 20.0 |

*Values in ppm with respect to trimethylsilane (TMS) at 0 ppm; referenced using an external sample of adamantane, setting is upfield resonance to 29.5 ppm.

Table 31 lists the $^{19}$F NMR chemical shifts for atorvastatin dibenzylamine and hydrates thereof:

TABLE 31

ATORVASTATIN DIBENZYLAMINE AND HYDRATES THEREOF

| Peak # | ppm* |
|---|---|
| 1 | −107.8 |

*Values in ppm with respect to CCl$_3$F at 0 ppm, referenced using an external standard of trifluoroacetic acid (50% V/V in water) at −76.54 ppm.

Table 32 lists the $^{13}$C NMR chemical shifts for atorvastatin erbumine and hydrates thereof:

TABLE 32

ATORVASTATIN ERBUMINE AND HYDRATES THEREOF

| Peak # | ppm* |
|---|---|
| 1 | 179.3 |
| 2 | 164.5 |
| 3 | 163.0 |
| 4 | 160.9 |
| 5 | 141.3 |
| 6 | 140.9 |
| 7 | 135.3 |
| 8 | 134.5 |
| 9 | 132.8 |
| 10 | 129.0 |
| 11 | 127.7 |
| 12 | 124.5 |
| 13 | 121.8 |
| 14 | 120.2 |
| 15 | 116.5 |
| 16 | 115.5 |
| 17 | 112.4 |
| 18 | 71.3 |
| 19 | 50.3 |
| 20 | 47.7 |
| 21 | 42.6 |
| 22 | 41.0 |
| 23 | 28.5 |
| 24 | 26.4 |
| 25 | 22.6 |
| 26 | 21.6 |

*Values in ppm with respect to trimethylsilane (TMS) at 0 ppm; referenced using an external sample of adamantane, setting is upfield resonance to 29.5 ppm.

Table 33 lists individual $^{13}$C NMR chemical shifts for atorvastatin erbumine and hydrates thereof:

TABLE 33

ATORVASTATIN ERBUMINE AND HYDRATES THEREOF

| Peak # | ppm* |
|---|---|
| 1 | 179.3 |
| 2 | 164.5 |
| 3 | 163.0 |
| 4 | 160.9 |
| 23 | 28.5 |
| 24 | 26.4 |
| 25 | 22.6 |
| 26 | 21.6 |

*Values in ppm with respect to trimethylsilane (TMS) at 0 ppm; referenced using an external sample of adamantane, setting is upfield resonance to 29.5 ppm.

Table 34 lists the $^{19}$F NMR chemical shifts for atorvastatin erbumine and hydrates thereof:

TABLE 34

ATORVASTATIN ERBUMINE AND HYDRATES THEREOF

| Peak # | ppm* |
|---|---|
| 1 | −110.4 |

*Values in ppm with respect to CCl$_3$F at 0 ppm, referenced using an external standard of trifluoroacetic acid (50% V/V in water) at −76.54 ppm.

Table 35 lists the $^{13}$C NMR chemical shifts for atorvastatin morpholine and hydrates thereof:

TABLE 35

ATORVASTATIN MORPHOLINE AND HYDRATES THEREOF

| Peak # | ppm* |
|---|---|
| 1 | 179.3 |
| 2 | 165.9 |
| 3 | 162.7 |
| 4 | 160.5 |
| 5 | 139.6 |
| 6 | 137.8 |
| 7 | 134.3 |
| 8 | 131.2 |
| 9 | 129.6 |
| 10 | 128.7 |
| 11 | 127.4 |
| 12 | 122.9 |
| 13 | 120.8 |
| 14 | 117.9 |
| 15 | 116.3 |
| 16 | 70.8 |
| 17 | 69.5 |
| 18 | 63.4 |
| 19 | 42.4 |
| 20 | 41.2 |
| 21 | 40.5 |
| 22 | 24.8 |
| 23 | 20.6 |

*Values in ppm with respect to trimethylsilane (TMS) at 0 ppm; referenced using an external sample of adamantane, setting is upfield resonance to 29.5 ppm.

Table 36 lists individual $^{13}$C NMR chemical shifts for atorvastatin morpholine and hydrates thereof:

TABLE 36

ATORVASTATIN MORPHOLINE AND HYDRATES THEREOF

| Peak # | ppm* |
|---|---|
| 1 | 179.3 |
| 2 | 165.9 |
| 4 | 160.5 |
| 22 | 24.8 |
| 23 | 20.6 |

*Values in ppm with respect to trimethylsilane (TMS) at 0 ppm; referenced using an external sample of adamantane, setting is upfield resonance to 29.5 ppm.

Table 37 lists individual $^{19}$F NMR chemical shifts for atorvastatin morpholine and hydrates thereof:

TABLE 37

ATORVASTATIN MORPHOLINE AND HYDRATES THEREOF

| Peak # | ppm* |
|---|---|
| 1 | −117.6 |

*Values in ppm with respect to CCl$_3$F at 0 ppm, referenced using an external standard of trifluoroacetic acid (50% V/V in water) at −76.54 ppm.

Table 38 lists the $^{13}$C NMR chemical shifts for atorvastatin olamine and hydrates thereof:

TABLE 38

ATORVASTATIN OLAMINE AND HYDRATES THEREOF

| Peak # | ppm* |
|---|---|
| 1 | 182.0 |
| 2 | 178.9 |
| 3 | 165.4 |
| 4 | 161.6 |
| 5 | 159.5 |
| 6 | 137.4 |
| 7 | 134.8 |
| 8 | 133.8 |
| 9 | 131.0 |
| 10 | 128.7 |
| 11 | 128.0 |
| 12 | 127.0 |
| 13 | 123.1 |
| 14 | 122.6 |
| 15 | 121.9 |
| 16 | 120.9 |
| 17 | 120.1 |
| 18 | 117.3 |
| 19 | 115.6 |
| 20 | 114.3 |
| 21 | 66.5 |
| 22 | 66.0 |
| 23 | 65.2 |
| 24 | 58.5 |
| 25 | 58.2 |
| 26 | 51.1 |
| 27 | 47.8 |
| 28 | 46.0 |
| 29 | 43.9 |
| 30 | 42.4 |
| 31 | 41.3 |
| 32 | 40.6 |
| 33 | 39.8 |
| 34 | 25.7 |
| 35 | 23.1 |
| 36 | 21.1 |
| 37 | 20.7 |

*Values in ppm with respect to trimethylsilane (TMS) at 0 ppm; referenced using an external sample of adamantane, setting is upfield resonance to 29.5 ppm.

Table 39 lists the individual $^{13}$C NMR chemical shifts for atorvastatin olamine and hydrates thereof:

TABLE 39

ATORVASTATIN OLAMINE AND HYDRATES THEREOF

| Peak # | PPM# |
|---|---|
| 1 | 182.0 |
| 2 | 178.9 |
| 3 | 165.4 |
| 4 | 161.6 |
| 5 | 159.5 |
| 34 | 25.7 |
| 35 | 23.1 |
| 36 | 21.1 |
| 37 | 20.7 |

*Values in ppm with respect to trimethylsilane (TMS) at 0 ppm; referenced using an external sample of adamantane, setting is upfield resonance to 29.5 ppm.

Table 40 lists the $^{19}$F NMR chemical shifts for atorvastatin olamine and hydrates thereof:

TABLE 40

ATORVASTATIN OLAMINE AND HYDRATES THEREOF

| Peak # | ppm* |
|---|---|
| 1 | −118.7 |

*Values in ppm with respect to CCl$_3$F at 0 ppm, referenced using an external standard of trifluoroacetic acid (50% V/V in water) at −76.54 ppm.

Table 41 lists the $^{13}$C NMR chemical shifts for atorvastatin 2-amino-2-methyl-propan-1-ol and hydrates thereof:

TABLE 41

ATORVASTATIN 2-AMINO-2-METHYL-PROPAN-1-OL AND HYDRATES THEREOF

| Peak # | ppm* |
|---|---|
| 1 | 179.8 |
| 2 | 166.3 |
| 3 | 163.3 |
| 4 | 161.5 |
| 5 | 161.2 |
| 6 | 140.5 |
| 7 | 139.5 |
| 8 | 134.4 |
| 9 | 132.3 |
| 10 | 131.6 |
| 11 | 129.8 |
| 12 | 128.1 |
| 13 | 126.1 |
| 14 | 125.1 |
| 15 | 122.2 |
| 16 | 120.7 |
| 17 | 116.4 |
| 18 | 114.0 |
| 19 | 113.4 |
| 20 | 72.6 |
| 21 | 71.4 |
| 22 | 67.6 |
| 23 | 66.3 |
| 24 | 64.7 |
| 25 | 64.4 |
| 26 | 53.1 |
| 27 | 46.9 |
| 28 | 43.9 |
| 29 | 43.5 |
| 30 | 42.7 |
| 31 | 39.7 |
| 32 | 36.1 |
| 33 | 26.8 |
| 34 | 26.3 |
| 35 | 24.3 |
| 36 | 23.8 |
| 37 | 23.1 |
| 38 | 22.0 |
| 39 | 20.4 |

*Values in ppm with respect to trimethylsilane (TMS) at 0 ppm; referenced using an external sample of adamantane, setting is upfield resonance to 29.5 ppm.

Table 42 lists individual $^{13}$C NMR chemical shifts for atorvastatin 2-amino-2-methyl-propan-1-ol and hydrates thereof:

TABLE 42

ATORVASTATIN 2-AMINO-2-METHYL-PROPAN-1-OL AND HYDRATES THEREOF

| Peak # | ppm* |
|---|---|
| 1 | 179.8 |
| 2 | 166.3 |
| 3 | 163.3 |
| 38 | 22.0 |
| 39 | 20.4 |

*Values in ppm with respect to trimethylsilane (TMS) at 0 ppm; referenced using an external sample of adamantane, setting is upfield resonance to 29.5 ppm.

Table 43 lists the $^{19}$F NMR chemical shifts for atorvastatin 2-amino-2-methyl-propan-1-ol and hydrates thereof:

TABLE 43

ATORVASTATIN 2-AMINO-2-METHYL-PROPAN-1-OL AND HYDRATES THEREOF

| Peak # | ppm* |
|---|---|
| 1 | −113.6 |
| 2 | −116.5 |

*Values in ppm with respect to CCl$_3$F at 0 ppm, referenced using an external standard of trifluoroacetic acid (50% V/V in water) at −76.54 ppm.

Additionally, Form A & B atorvastatin benethamine, atorvastatin dibenzylamine, atorvastatin erbumine, atorvastatin morpholine, atorvastatin olamine, and atorvastatin 2-amino-2-methyl-propan-1-ol or a hydrate thereof of the aforementioned salts may be characterized by an x-ray powder diffraction pattern or a solid state $^{19}$F nuclear magnetic resonance spectrum. For example:

An atorvastatin ammonium or hydrate thereof having an x-ray powder diffraction pattern containing the following 2θ peaks measured using CuK$_\alpha$ radiation: 7.8, 8.8, 9.3, 9.9, 10.6, 12.4, and 19.5.

A Form A atorvastatin benethamine or hydrate thereof having an x-ray powder diffraction pattern containing the following 2θ peaks measured using CuK$_\alpha$ radiation: 4.7, 5.3, 9.5, 12.0, 15.6, 18.1, and 19.9, or a solid state $^{19}$F nuclear magnetic resonance having the following chemical shifts expressed in parts per million: −113.2 and −114.2.

A Form B atorvastatin benethamine or hydrate thereof having an x-ray powder diffraction pattern containing the following 2θ peaks measured using CuK$_\alpha$ radiation: 5.0, 7.1, 8.4, 10.0, 11.6, 12.6, 14.8, and 20.2, or a solid state $^{19}$F nuclear magnetic resonance having the following chemical shifts expressed in parts per million: −113.7 and −114.4.

A Form A atorvastatin benzathine or hydrate thereof having an x-ray powder diffraction pattern containing the following 2θ peaks measured using CuK$_\alpha$ radiation: 14.0 and 15.1.

A Form B atorvastatin benzathine or hydrate thereof having an x-ray powder diffraction pattern containing the following 2θ peaks measured using CuK$_\alpha$ radiation: 8.3, 10.2, 14.4, 15.8, 18.6, 21.8, and 23.3.

A Form C atorvastatin benzathine or hydrate thereof having an x-ray powder diffraction pattern containing the following 2θ peaks measured using CuK$_\alpha$ radiation: 3.9, 6.9, 7.9, 9.7, and 12.8.

An atorvastatin dibenzylamine or hydrate thereof having an x-ray powder diffraction pattern containing the following 2θ peaks measured using CuK$_\alpha$ radiation: 8.3, 18.7, 19.8, 20.7, 21.3, and 25.8, or a solid state $^{19}$F nuclear magnetic resonance having the following chemical shifts expressed in parts per million: −107.8.

A compound selected from the group consisting of:
(a) Form A atorvastatin diethylamine or hydrate thereof having an x-ray powder diffraction pattern containing the following 2θ peaks measured using CuK$_\alpha$ radiation: 17.0, 18.2, 20.0, 21.7, and 23.0; and
(b) Form B atorvastatin diethylamine or a hydrate thereof having an x-ray powder diffraction pattern containing the following 2θ peaks measured using CuK$_\alpha$ radiation: 6.1, 11.5, 15.3, 17.4, 20.5, 23.2, and 27.6.

An atorvastatin erbumine or a hydrate thereof having an x-ray powder diffraction pattern containing the following 2θ peaks measured using CuK$_\alpha$ radiation: 5.4, 7.3, 9.5, 17.8, 19.2, 20.0, 22.2, and 24.2, or a solid state $^{19}$F nuclear magnetic resonance having the following chemical shifts expressed in parts per million: −110.4.

An atorvastatin L-lysine or a hydrate thereof having an x-ray powder diffraction pattern containing the following 2θ peaks measured using CuK$_\alpha$ radiation: 6.7, 9.8, 17.1, and 24.0.

An atorvastatin morpholine or a hydrate thereof having an x-ray powder diffraction pattern containing the following 2θ peaks measured using CuK$_\alpha$ radiation: 9.7, 16.0, 18.9, 19.6, 20.8, 22.1, 23.9, and 25.0, or a solid state $^{19}$F nuclear magnetic resonance having the following chemical shifts expressed in parts per million: −117.6.

An atorvastatin olamine or a hydrate thereof having an x-ray powder diffraction pattern containing the following 2θ peaks measured using CuK$_\alpha$ radiation: 8.5, 9.8, 17.4, 18.6, 20.9, 22.5, and 24.1, or a solid state $^{19}$F nuclear magnetic resonance having the following chemical shifts measured in parts per million: −118.7.

An atorvastatin piperazine or a hydrate thereof having an x-ray powder diffraction pattern containing the following 2θ peaks measured using CuK$_\alpha$ radiation: 7.8, 9.3, 11.8, 16.1, and 19.7.

An atorvastatin sodium or a hydrate thereof having an x-ray powder diffraction pattern containing the following 2θ peaks measured using CuK$_\alpha$ radiation: 3.4, 4.9, 7.6, 8.0, 9.9, 18.9, and 19.7.

An atorvastatin 2-amino-2-methylpropan-1-ol or a hydrate thereof having an x-ray powder diffraction pattern containing the following 2θ peaks measured using CuK$_\alpha$ radiation: 4.2, 8.3, 16.0, 17.5, 18.3, 19.4, and 19.7, or a solid state $^{19}$F nuclear magnetic resonance having the following chemical shifts measured in parts per million: −113.6 and −116.5.

The salt forms of atorvastatin of the present invention, regardless of the extent of hydration and/or solvation having equivalent x-ray powder diffractograms, or SSNMR, are within the scope of the present invention.

The new salt forms of atorvastatin described herein have advantageous properties. For example, the benethamine, benzathine, dibenzylamine, diethylamine, erbumine, and morpholine salts were determined to be anhydrous, high melting as well as considered to be non-hygroscopic compounds. The olamine and 2-amino-2-methylpropan-1-ol salts were determined to be anhydrous and high melting as well. Also, the diethylamine, erbumine, morpholine, olamine, and 2-amino-2-methylpropan-1-ol salts of atorvastatin exhibited higher aqueous solubility compared to Form I atorvastatin calcium (disclosed in U.S. Pat. No. 5,969,156).

The present invention provides a process for the preparation of the salt forms of atorvastatin which comprises preparing a solution of atorvastatin free acid (U.S. Pat. No. 5,213,995) in one of the following solvents: acetone, acetonitrile, THF, 1:1 acetone/water (v/v), isopropanol (IPA), or chloroform. The cationic counterion solutions were prepared using either 0.5 or 1.0 equivalent in the same solvent. Water was added to some counterions to increase their solubility. The atorvastatin free acid solution was added to the counterion solution while stirring. The reaction was stirred for at least 48 hours at ambient temperature. Samples containing solids were vacuum filtered, washed with the reaction solvent, and air-dried overnight at ambient conditions. If precipitation was not present after ~2 weeks, the solution was slowly evaporated. All samples were stored at ambient temperature and characterized as described hereinafter.

TABLE 44

Structure of Counterions used in the preparation of Atorvastatin salts.

| Structure | Name | Common Name |
|---|---|---|
| $^+NH_4$ | Ammonium | Ammonium |
| (N-benzyl-2-phenylethylamine structure) | N-benzyl-2-Phneylethylamine | Benethamine |
| (N,N'-dibenzylethylenediamine structure) | N,N'-Bis(phenylmethyl)-1,2-ethanediamine | Benzathine |
| (dibenzylamine structure) | N-(Phenylmethyl)benzenemethanamine | Dibenzylamine |
| (diethylamine structure) | N-Ethylethanamine | Diethylamine |
| (tert-butylamine structure) | tert-butylamine | Erbumine |

TABLE 44-continued

Structure of Counterions used in the preparation of Atorvastatin salts.

| Structure | Name | Common Name |
|---|---|---|
| H₂N—CH—CO₂H / (CH₂)₄ / NH₂ | (S)-2,6-diaminohexanoic acid | L-Lysine |
| (morpholine ring structure) | Tetrahydro-2H-1,4-oxazine | Morpholine |
| HO-CH₂-CH₂-NH₂ | 2-aminoethanol | Olamine |
| Na | Sodium | Sodium |
| (piperazine ring structure) | Hexahydropyrazine | Piperazine |
| (HOCH₂-C(CH₃)₂-NH₂) | 2,2-Diethylethanolamine | 2-amino-2methylpropan-1-ol |

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from two or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, retention enemas, and emulsions, for example water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.5 mg to 100 mg, preferably 2.5 mg to 80 mg according to the particular application and the potency of the active component. The composition can, if desired, also contain other compatible therapeutic agents.

In therapeutic use as hypolipidemic and/or hypocholesterolemic agents and agents to treat osteoporosis, benign prostatic hyperplasia, and Alzheimer's disease, the salt forms of atorvastatin utilized in the pharmaceutical method of this invention are administered at the initial dosage of about 2.5 mg to about 80 mg daily. A daily dose range of about 2.5 mg to about 20 mg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following nonlimiting examples illustrate the inventors' preferred methods for preparing the compounds of the invention.

Example 1

[R—(R*,R*)]-2-(4-Fluorophenyl)-β,δ-dihydroxy-5-(1-methylethyl)-3-phenyl-4-[(phenylamino)carbonyl]-1H-pyrrole-1-heptanoic acid, ammonium salt (atorvastatin ammonium)

The ammonium salt of atorvastatin was synthesized by preparing a stock solution of the free acid of atorvastatin (U.S. Pat. No. 5,273,995) in acetonitrile (ACN) (0.634 g in 25 mL of ACN). A solution was prepared by dissolving 12.04 mg of ammonium hydroxide (1.0 equivalents) in acetonitrile (0.5 mL). The stock solution of atorvastatin free acid (2.24 mL) was added to the counterion solution with stirring. If a gel formed, additional acetonitrile and water was added as necessary. After 2 days of stirring at ambient temperature, the solids were isolated by vacuum filtration using a 0.45 μm nylon 66 membrane filter. The solids were rinsed with acetonitrile and air dried at ambient conditions to afford atorvastatin ammonium.

Example 2

[R—(R*,R*)]-2-(4-Fluorophenyl)-β,δ-dihydroxy-5-(1-methylethyl)-3-phenyl-4-[(phenylamino)carbonyl]-1H-pyrrole-1-heptanoic acid, N-benzyl-2-phenylethylamine (atorvastatin benethamine)

Method A:
The benethamine salt of atorvastatin (Form A) was synthesized by preparing a stock solution of the free acid of atorvastatin (U.S. Pat. No. 5,273,995) in acetonitrile (1 g in 40 mL of ACN). A solution of N-benzyl-2-phenylethylamine (benethamine) was prepared by dissolving 378.59 mg (1.0 equivalents) in acetonitrile (10 mL). The stock solution of atorvastatin free acid was added to the counterion solution with stirring. Over time, an additional 40 mL of acetonitrile was added to prevent the formation of a gel. After 5 days of stirring at ambient temperature, the solids were isolated by vacuum filtration using a Buchner funnel fitted with a paper filter (#2 Whatman). The solids were rinsed with acetonitrile (75 mL), and placed in a 25° C. oven under nitrogen to dry overnight to afford atorvastatin benethamine Form A.

Method B:
The benethamine salt of atorvastatin (Form B) was synthesized by preparing a stock solution of the free acid of atorvastatin (U.S. Pat. No. 5,273,995) in 2-propanol (IPA) (1 g in 40 mL of IPA). A solution of N-benzyl-2-phenylethylamine (benethamine) was prepared by dissolving 388.68 mg (1.1 equivalents) in 2-propanol (100 mL). The stock solution of atorvastatin free acid was added to the counterion solution with stirring. Seed crystals of the benethamine salt were added. The mixture was reduced to a wet solid under a nitrogen bleed, and the resulting solids were slurried in 2-propanol (40 mL). After 7 days of stirring at ambient temperature, the solids were isolated by vacuum filtration using a Buchner funnel fitted with a paper filter (#2 Whatman). The solids were rinsed with 2-propanol (25 mL), and placed in a 25° C. oven under nitrogen to dry overnight to afford atorvastatin benethamine Form B.

Example 3

[R—(R*,R*)]-2-(4-Fluorophenyl)-β,δ-dihydroxy-5-(1-methylethyl)-3-phenyl-4-[(phenylamino)carbonyl]-1H-pyrrole-1-heptanoic acid,N,N$^1$-bis(phenylmethyl)-1,2-ethanediamine (atorvastatin benzathine)

Method A:
The benzathine salt of atorvastatin (Form A) was synthesized by preparing a stock solution of the free acid of atorvastatin (U.S. Pat. No. 5,273,995) in acetonitrile (1 g in 40 mL of ACN). A solution of N,N'-bis(phenylmethyl)-1,2-ethanediamine (benzathine) was prepared by dissolving 220.64 mg (0.5 equivalents) in acetonitrile (80 mL) and water (20 mL). The stock solution of atorvastatin free acid was added to the counterion solution with stirring. After 2 days of stirring at ambient temperature, the solids were isolated by vacuum filtration using a Buchner funnel fitted with a paper filter (#2 Whatman). The solids were rinsed with acetonitrile (75 mL), and placed in a 25° C. oven under nitrogen to dry overnight to afford benzathine Form A.

Method B:
The benzathine salt of atorvastatin (Form B) was synthesized by preparing a stock solution of the free acid of atorvastatin (U.S. Pat. No. 5,273,995) in acetonitrile (1 g in 40 mL of ACN). A solution of N,N'-bis(phenylmethyl-1,2-ethanediamine (benzathine) was prepared by dissolving 220.64 mg (0.5 equivalents) in acetonitrile (80 mL) and water (20 mL). The stock solution of atorvastatin free acid was added to the counterion solution with stirring. After 2 days of stirring at ambient temperature, the solids were isolated by vacuum filtration using a Buchner funnel fitted with a paper filter (#2 Whatman). The solids were rinsed with acetonitrile (75 mL) to afford atorvastatin benzathine Form B. Note that this procedure is the same as above except that the sample was not oven dried.

Method C:

The benzathine salt of atorvastatin (Form C) was synthesized by adding Form A atorvastatin benzathine to 3 mL of deionized water in excess of its solubility. The slurry was stirred at room temperature for 2 days, isolated by vacuum filtration, and dried under ambient conditions to yield atorvastatin benzathine Form C.

Example 4

[R—(R*,R*)]-2-(4-Fluorophenyl)-β,δ-dihydroxy-5-(1-methylethyl)-3-phenyl-4-[(phenylamino)carbonyl]-1H-pyrrole-1-heptanoic acid,N-(phenylmethyl) benzenemethanamine (atorvastatin dibenzylamine)

The dibenzylamine salt of atorvastatin was synthesized by preparing a stock solution of the free acid of atorvastatin (U.S. Pat. No. 5,273,995) in acetonitrile (1 g in 40 mL of ACN). A solution of dibenzylamine was prepared by dissolving 351.05 mg (1.0 equivalents) in acetonitrile (100 mL). The stock solution of atorvastatin free acid was added to the counterion solution with stirring. Over time, additional acetonitrile was added to prevent formation of a gel (100 mL), and the solid was allowed to stir. After 4 days of stirring at ambient temperature, the solids were isolated by vacuum filtration using a Buchner funnel fitted with a paper filter (#2 Whatman). The solids were rinsed with acetonitrile (75 mL), and placed in a 25° C. oven under nitrogen to dry overnight to afford atorvastatin dibenzylamine.

Example 5

[R—(R*,R*)]-2-(4-Fluorophenyl)-β,δ-dihydroxy-5-(1-methylethyl)-3-phenyl-4-[(phenylamino)carbonyl]-1H-pyrrole-1-heptanoic acid,N-ethylethanamine (atorvastatin diethylamine)

Method A:

The diethylamine salt of atorvastatin (Form A) was synthesized by preparing a stock solution of the free acid of atorvastatin (U.S. Pat. No. 5,273,995) in acetonitrile (1 g in 40 mL of ACN). A solution of diethylamine was prepared by dissolving 132.33 mg (1.0 equivalents) in acetonitrile (20 mL). The stock solution of atorvastatin free acid was added to the counterion solution with stirring. Over time, an additional 40 mL of acetonitrile was added to prevent the formation of a gel. After 5 days of stirring at ambient temperature, the solids were isolated by vacuum filtration using a Buchner funnel fitted with a paper filter (#2 Whatman). The solids were rinsed with acetonitrile (75 mL), and placed in a 25° C. oven under nitrogen to dry overnight to afford atorvastatin diethylamine Form A.

Method B:

The diethylamine salt of atorvastatin (Form B) was synthesized by preparing a stock solution of the free acid of atorvastatin (U.S. Pat. No. 5,273,995) in acetonitrile (1 g in 40 mL of ACN). A solution of diethylamine was prepared by dissolving 132.33 mg (1.0 equivalents) in acetonitrile (20 mL). The stock solution of atorvastatin free acid was added to the counterion solution with stirring. Over time, an additional 40 mL of acetonitrile was added to prevent the formation of a gel. After 5 days of stirring at ambient temperature, the solids were isolated by vacuum filtration using a Buchner funnel fitted with a paper filter (#2 Whatman). The solids were rinsed with acetonitrile (75 mL) to afford atorvastatin diethylamine Form B. Note that this procedure is the same as above except that the sample was not oven dried.

Example 6

[R—(R*,R*)]-2-(4-Fluorophenyl)-β,δ-dihydroxy-5-(1-methylethyl)-3-phenyl-4-[(phenylamino)carbonyl]-1H-pyrrole-1-heptanoic acid, tertiary-butylamine (atorvastatin erbumine)

The erbumine salt of atorvastatin was synthesized by preparing a stock solution of the free acid of atorvastatin (U.S. Pat. No. 5,273,995) in acetonitrile (1 g in 40 mL of ACN). A solution of tert-butylamine (erbumine) was prepared by dissolving 128.00 mg (1.0 equivalents) in acetonitrile (10 mL). The stock solution of atorvastatin free acid was added to the counterion solution with stirring. Over time, an additional 120 mL of acetonitrile was added to prevent the formation of a gel. After 5 days of stirring at ambient temperature, the solids were isolated by vacuum filtration using a Buchner funnel fitted with a paper filter (#2 Whatman). The solids were rinsed with acetonitrile (75 mL), and placed in a 25° C. oven under nitrogen to dry overnight to afford atorvastatin erbumine.

Example 7

[R—(R*,R*)]-2-(4-Fluorophenyl)-β,δ-dihydroxy-5-(1-methylethyl)-3-phenyl-4-[(phenylamino)carbonyl]-1H-pyrrole-1-heptanoic acid, L-lysine (atorvastatin L-lysine)

The L-lysine salt of atorvastatin was synthesized by preparing a stock solution of the free acid of atorvastatin (U.S. Pat. No. 5,273,995) in isopropyl alcohol (IPA) (2.577 g in 50 mL of IPA). A solution of L-lysine was prepared by dissolving 28.0 mg (1.0 equivalents) in isopropyl alcohol (1 mL). The stock solution of atorvastatin free acid (2.08 mL) was added to the counterion solution with stirring. After 7 days of stirring at ambient temperature, the solids were isolated by vacuum filtration using a 0.45 µm nylon 66 membrane filter. The solids were rinsed with IPA and allowed to air dry at ambient temperature to afford L-lysine.

Example 8

[R—(R*,R*)]-2-(4-Fluorophenyl)-β,δ-dihydroxy-5-(1-methylethyl)-3-phenyl-4-[(phenylamino)carbonyl]-1H-pyrrole-1-heptanoic acid, tetrahydro-2H-1, 4-oxazine (atorvastatin morpholine)

The morpholine salt of atorvastatin was synthesized by preparing a stock solution of the free acid of atorvastatin (U.S. Pat. No. 5,273,995) in acetonitrile (1 g in 40 mL of ACN). A solution of morpholine was prepared by dissolving 160.28 mg (1.1 equivalents) in acetonitrile (100 mL). The stock solution of atorvastatin free acid was added to the counterion solution with stirring. No salt formed, so the solution was evaporated under $N_2$ until a white solid formed. Acetonitrile was then added to the solid (50 mL), and the solid was allowed to stir. After 3 days of stirring at ambient temperature, the solids were isolated by vacuum filtration using a Buchner funnel fitted with a paper filter (#2 Whatman). The solids were rinsed with acetonitrile (25 mL), and placed in a 25° C. oven under nitrogen to dry overnight to afford atorvastatin morpholine.

Example 9

[R—(R*,R*)]-2-(4-Fluorophenyl)-β,δ-dihydroxy-5-(1-methylethyl)-3-phenyl-4-[(phenylamino)carbonyl]-1H-pyrrole-1-heptanoic acid, 2-aminoethanol (atorvastatin olamine)

Method A—

The olamine salt of atorvastatin was synthesized by preparing a stock solution of the free acid of atorvastatin (U.S. Pat. No. 5,273,995) in acetonitrile (0.8 g in 25 mL of ACN). A solution of olamine was prepared by dissolving 15.0 mg of olamine (~2.7 equivalents) in 0.5 mL of acetonitrile. The stock solution of atorvastatin free acid (3.0 mL) was added to the counterion solution with stirring. If a gel formed, additional acetonitrile was added as necessary. After 6 days of stirring at ambient temperature, the solids were isolated by vacuum filtration using a 0.45 µm nylon 66 membrane filter. The solids were rinsed with acetonitrile and air dried at ambient conditions to afford atorvastatin olamine.

Method B—

The olamine salt of atorvastatin was synthesized by preparing a stock solution of the free acid of atorvastatin (U.S. Pat. No. 5,273,995) in acetonitrile (1 g in 40 mL of ACN). A solution of 2-aminoethanol (olamine) was prepared by dissolving 139.77 mg (1.1 equivalents) in acetonitrile (100 mL). The stock solution of atorvastatin free acid was added to the counterion solution with stirring. Seed crystals of the olamine salt were added. Over time, additional acetonitrile was added to aid in stirring (300 mL), and the solid was allowed to stir. After 4 days of stirring at ambient temperature, the solids were isolated by vacuum filtration using a Buchner funnel fitted with a paper filter (#2 Whatman). The solids were rinsed with acetonitrile (75 mL), and placed in a 25° C. oven under nitrogen to dry for two days to afford atorvastatin olamine.

Example 10

[R—(R*,R*)]-2-(4-Fluorophenyl)-β,δ-dihydroxy-5-(1-methylethyl)-3-phenyl-4-[(phenylamino)carbonyl]-1H-pyrrole-1-heptanoic acid, piperazine (atorvastatin piperazine)

The piperazine salt of atorvastatin was synthesized by preparing a stock solution of the free acid of atorvastatin (U.S. Pat. No. 5,273,995) in isopropyl alcohol (2.577 g in 50 mL of IPA). A solution of piperazine was prepared by dissolving 14.4 mg (1.0 equivalents) in isopropyl alcohol (1 mL). The stock solution of atorvastatin free acid (1.85 mL) was added to the counterion solution with stirring. After 7 days of stirring at ambient temperature, the solids were isolated by vacuum filtration using a 0.45 µm nylon 66 membrane filter. The solids were rinsed with isopropyl alcohol and air dried at ambient conditions to afford atorvastatin piperazine.

Example 11

[R—(R*,R*)]-2-(4-Fluorophenyl)-β,δ-dihydroxy-5-(1-methylethyl)-3-phenyl-4-[(phenylamino)carbonyl]-1H-pyrrole-1-heptanoic acid, sodium (atorvastatin sodium)

The sodium salt of atorvastatin was synthesized by preparing a stock solution of the free acid of atorvastatin (U.S. Pat. No. 5,273,995) in acetonitrile (0.634 g in 25 mL of ACN). A solution was prepared by dissolving 2.67 mg of sodium hydroxide (1.0 equivalents) in 0.5 mL of acetonitrile and 0.05 mL of water. The stock solution of atorvastatin free acid (1.55 mL) was added to the counterion solution with stirring. If a gel formed, additional acetonitrile and water was added as necessary. After 6 days of stirring at ambient temperature, the solids were isolated by vacuum filtration using a 0.45 µm nylon 66 membrane filter. The solids were rinsed with acetonitrile and air dried at ambient conditions to afford atorvastatin sodium.

Example 12

[R—(R*,R*)]-2-(4-Fluorophenyl)-β,δ-dihydroxy-5-(1-methylethyl)-3-phenyl-4-[(phenylamino)carbonyl]-1H-pyrrole-1-heptanoic acid, 2-amino-2-methylpropan-1-ol (atorvastatin 2-amino-2-methylpropan-1-ol)

Method A—

The 2-amino-2-methylpropan-1-ol salt of atorvastatin was synthesized by preparing a stock solution of the free acid of atorvastatin (U.S. Pat. No. 5,273,995) in acetonitrile (0.8 g in 25 mL of ACN). A solution of 2-amino-2-methylpropan-1-ol was prepared by dissolving 6.1 mg of 2-amino-2-methylpropan-1-ol (1 equivalents) in 0.5 mL of acetonitrile. The stock solution of atorvastatin free acid (1.21 mL) was added to the counterion solution with stirring. If a gel formed, additional acetonitrile was added as necessary. After 6 days of stirring at ambient temperature, the solids were isolated by vacuum filtration using a 0.45 µm nylon 66 membrane filter. The solids were rinsed with acetonitrile and air dried at ambient conditions to afford atoravastatin 2-amino-2-methylpropan-1-ol.

Method B—

The 2-amino-2-methylpropan-1-ol salt of atorvastatin was synthesized by preparing a stock solution of the free acid of atorvastatin (U.S. Pat. No. 5,273,995) in acetonitrile (1 g in 40 mL of ACN). A solution of 2-amino-2-methylpropan-1-ol was prepared by dissolving 173.08 mg (1.1 equivalents) in acetonitrile (100 mL). The stock solution of atorvastatin free acid was added to the counterion solution with stirring. Seed crystals of the 2-amino-2-methylpropan-1-ol salt were added. Over time, additional acetonitrile was added to aid in stirring (100 mL), and the solid was allowed to stir. After 4 days of stirring at ambient temperature, the solids were isolated by vacuum filtration using a Buchner funnel fitted with a paper filter (#2 Whatman). The solids were rinsed with acetonitrile (75 mL), and placed in a 25° C. oven under nitrogen to dry for two days to afford atorvastatin 2-amino-2-methylpropan-1-ol.

What is claimed is:

1. A Form A atorvastatin benzathine having an x-ray powder diffraction pattern containing the following 2θ peaks measured using $CuK_\alpha$ radiation: 14.0 and 15.1.

2. A Form B atorvastatin benzathine having an x-ray powder diffraction pattern containing the following 2θ peaks measured using $CuK_\alpha$ radiation: 8.3, 10.2, 14.4, 15.8, 18.6, 21.8, and 23.3.

3. A Form C atorvastatin benzathine having an x-ray powder diffraction pattern containing the following 2θ peaks measured using $CuK_\alpha$ radiation: 3.9, 6.9, 7.9, 9.7, and 12.8.

4. A Form A atorvastatin benzathine having an x-ray powder diffraction pattern containing the following 2θ peaks measured using CuK$_\alpha$ radiation: 9.1, 14.0, 15.1, 15.5, 16.1, 16.4, 18.2, 19.1, 19.6, 20.5, 21.3, 22.1, 22.5, 23.0, 25.2, 25.9, 26.1, 26.5, 28.0, and 28.6.

5. A Form B atorvastatin benzathine having an x-ray powder diffraction pattern containing the following 2θ peaks measured using CuK$_\alpha$ radiation: 8.3, 9.1, 10.2, 11.7, 13.2, 14.4, 15.8, 16.6, 17.1, 18.6, 19.1, 19.4, 19.7, 20.6, 20.9, 21.4, 21.8, 22.3, 22.6, 23.3, 23.5, 24.3, 25.0, 26.5, 26.8, 27.4, 27.9, 28.2, 28.9, 29.1, and 29.7.

6. A Form C atorvastatin benzathine having an x-ray powder diffraction pattern containing the following 2θ peaks measured using CuK$_\alpha$ radiation: 3.9, 6.9, 7.9, 9.7, 11.9, 12.8, 13.2, 15.5, 16.3, 16.8, 17.2, 18.9, 19.5, 19.9, 20.4, 20.7, 21.4, 23.0, 23.4, 24.0, 24.3, 24.6, 25.9, and 26.2.

* * * * *